(12) United States Patent
Robinson et al.

(10) Patent No.: US 9,012,524 B2
(45) Date of Patent: Apr. 21, 2015

(54) HYDROMETHANATION OF A CARBONACEOUS FEEDSTOCK

(71) Applicant: GreatPoint Energy, Inc., Cambridge, MA (US)

(72) Inventors: Earl T. Robinson, Lakeland, FL (US); Pattabhi K. Raman, Kildeer, IL (US)

(73) Assignee: GreatPoint Energy, Inc., Cambridge, MA (US)

( * ) Notice: Subject to any disclaimer, the term of this patent is extended or adjusted under 35 U.S.C. 154(b) by 0 days.

(21) Appl. No.: 13/644,207

(22) Filed: Oct. 3, 2012

(65) Prior Publication Data

US 2013/0172640 A1     Jul. 4, 2013

Related U.S. Application Data

(60) Provisional application No. 61/544,029, filed on Oct. 6, 2011.

(51) Int. Cl.
| | | |
|---|---|---|
| *C07C 27/00* | (2006.01) | |
| *C07C 1/20* | (2006.01) | |
| *C07C 1/22* | (2006.01) | |
| *C10L 3/08* | (2006.01) | |
| *C10J 3/48* | (2006.01) | |

(52) U.S. Cl.
CPC ............. *C07C 1/22* (2013.01); *C10L 2290/141* (2013.01); *C10L 2290/04* (2013.01); *C10L 2290/10* (2013.01); *C10L 2290/06* (2013.01); *C10L 2290/148* (2013.01); *C10L 2290/145* (2013.01); *C10L 2290/545* (2013.01); *C10L 3/08* (2013.01); *C10J 3/482* (2013.01); *C10J 2300/093* (2013.01); *C10J 2300/0959* (2013.01); *C10J 2300/0976* (2013.01); *C10J 2300/0986* (2013.01); *C10J 2300/1662* (2013.01); *C10J 2300/1807* (2013.01); *C10J 2300/1823* (2013.01)

(58) Field of Classification Search
USPC ........................................................ 585/264
See application file for complete search history.

(56) References Cited

U.S. PATENT DOCUMENTS

| | | | |
|---|---|---|---|
| 2,605,215 | A | 7/1952 | Coghlan |
| 2,694,623 | A | 11/1954 | Welty, Jr. et al. |
| 2,791,549 | A | 5/1957 | Jahnig |
| 2,813,126 | A | 11/1957 | Tierney |
| 2,860,959 | A | 11/1958 | Pettyjohn et al. |

(Continued)

FOREIGN PATENT DOCUMENTS

| | | |
|---|---|---|
| CA | 966660 | 4/1975 |
| CA | 1003217 | 1/1977 |

(Continued)

OTHER PUBLICATIONS

U.S. Appl. No. 12/778,538, filed May 12, 2010, Robinson, et al.

(Continued)

*Primary Examiner* — In Suk Bullock
*Assistant Examiner* — Youngsul Jeong
(74) *Attorney, Agent, or Firm* — McDonnell Boehnen Hulbert & Berghoff LLP

(57) ABSTRACT

The present invention relates generally to processes for hydromethanating a carbonaceous feedstock in a hydromethanation reactor to a methane product stream and a char by-product, and more specifically to removal of the char by-product from the hydromethanation reactor.

16 Claims, 3 Drawing Sheets

(56) References Cited

U.S. PATENT DOCUMENTS

| | | |
|---|---|---|
| 2,886,405 A | 5/1959 | Benson et al. |
| 3,034,848 A | 5/1962 | King |
| 3,114,930 A | 12/1963 | Oldham et al. |
| 3,150,716 A | 9/1964 | Strelzoff et al. |
| 3,164,330 A | 1/1965 | Neidl |
| 3,351,563 A | 11/1967 | Negra et al. |
| 3,435,590 A | 4/1969 | Smith |
| 3,531,917 A | 10/1970 | Grunewald et al. |
| 3,544,291 A | 12/1970 | Schlinger et al. |
| 3,594,985 A | 7/1971 | Ameen et al. |
| 3,615,300 A | 10/1971 | Holm et al. |
| 3,689,240 A | 9/1972 | Aldridge et al. |
| 3,740,193 A | 6/1973 | Aldridge et al. |
| 3,746,522 A | 7/1973 | Donath |
| 3,759,036 A | 9/1973 | White |
| 3,779,725 A | 12/1973 | Hegarty et al. |
| 3,814,725 A | 6/1974 | Zimmerman et al. |
| 3,817,725 A | 6/1974 | Sieg et al. |
| 3,828,474 A | 8/1974 | Quartulli |
| 3,833,327 A | 9/1974 | Pitzer et al. |
| 3,847,567 A | 11/1974 | Kalina et al. |
| 3,876,393 A | 4/1975 | Kasai et al. |
| 3,904,386 A | 9/1975 | Graboski et al. |
| 3,915,670 A | 10/1975 | Lacey et al. |
| 3,920,229 A | 11/1975 | Piggott |
| 3,929,431 A | 12/1975 | Koh et al. |
| 3,958,957 A | 5/1976 | Koh et al. |
| 3,966,875 A | 6/1976 | Bratzler et al. |
| 3,969,089 A | 7/1976 | Moss et al. |
| 3,971,639 A | 7/1976 | Matthews |
| 3,972,693 A | 8/1976 | Wiesner et al. |
| 3,975,168 A | 8/1976 | Gorbaty |
| 3,985,519 A | 10/1976 | Kalina et al. |
| 3,989,811 A | 11/1976 | Hill |
| 3,996,014 A | 12/1976 | Muller et al. |
| 3,998,607 A | 12/1976 | Wesswlhoft et al. |
| 3,999,607 A | 12/1976 | Pennington et al. |
| 4,005,996 A | 2/1977 | Hausberger et al. |
| 4,011,066 A | 3/1977 | Bratzler et al. |
| 4,017,272 A | 4/1977 | Anwer et al. |
| 4,021,370 A | 5/1977 | Harris et al. |
| 4,025,423 A | 5/1977 | Stonner et al. |
| 4,044,098 A | 8/1977 | Miller et al. |
| 4,046,523 A | 9/1977 | Kalina et al. |
| 4,052,176 A | 10/1977 | Child et al. |
| 4,053,554 A | 10/1977 | Reed et al. |
| 4,057,512 A | 11/1977 | Vadovic et al. |
| 4,069,304 A | 1/1978 | Starkovich et al. |
| 4,077,778 A | 3/1978 | Nahas et al. |
| 4,091,073 A | 5/1978 | Winkler |
| 4,092,125 A | 5/1978 | Stambaugh et al. |
| 4,094,650 A | 6/1978 | Koh et al. |
| 4,100,256 A | 7/1978 | Bozzelli et al. |
| 4,101,449 A | 7/1978 | Noda et al. |
| 4,104,201 A | 8/1978 | Banks et al. |
| 4,113,615 A | 9/1978 | Gorbaty |
| 4,116,996 A | 9/1978 | Huang |
| 4,118,204 A | 10/1978 | Eakman et al. |
| 4,152,119 A | 5/1979 | Schulz |
| 4,157,246 A | 6/1979 | Eakman et al. |
| 4,159,195 A | 6/1979 | Clavenna |
| 4,162,902 A | 7/1979 | Wiesner et al. |
| 4,173,465 A | 11/1979 | Meissner et al. |
| 4,189,307 A | 2/1980 | Marion |
| 4,193,771 A | 3/1980 | Sharp et al. |
| 4,193,772 A | 3/1980 | Sharp |
| 4,200,439 A | 4/1980 | Lang |
| 4,204,843 A | 5/1980 | Neavel |
| 4,211,538 A | 7/1980 | Eakman et al. |
| 4,211,669 A | 7/1980 | Eakman et al. |
| 4,219,338 A | 8/1980 | Wolfs et al. |
| 4,223,728 A | 9/1980 | Pegg |
| 4,225,457 A | 9/1980 | Schulz |
| 4,235,044 A | 11/1980 | Cheung |
| 4,243,639 A | 1/1981 | Haas et al. |
| 4,249,471 A | 2/1981 | Gunnerman |
| 4,252,771 A | 2/1981 | Lagana et al. |
| 4,260,421 A | 4/1981 | Brown et al. |
| 4,265,868 A | 5/1981 | Kamody |
| 4,270,937 A | 6/1981 | Adler et al. |
| 4,284,416 A | 8/1981 | Nahas |
| 4,292,048 A | 9/1981 | Wesselhoft et al. |
| 4,298,584 A | 11/1981 | Makrides |
| 4,315,753 A | 2/1982 | Bruckenstein et al. |
| 4,315,758 A | 2/1982 | Patel et al. |
| 4,318,712 A | 3/1982 | Lang et al. |
| 4,322,222 A | 3/1982 | Sass |
| 4,330,305 A | 5/1982 | Kuessner et al. |
| 4,331,451 A | 5/1982 | Isogaya et al. |
| 4,334,893 A | 6/1982 | Lang |
| 4,336,034 A | 6/1982 | Lang et al. |
| 4,336,233 A | 6/1982 | Appl et al. |
| 4,341,531 A | 7/1982 | Duranleau et al. |
| 4,344,486 A | 8/1982 | Parrish |
| 4,347,063 A | 8/1982 | Sherwood et al. |
| 4,348,486 A | 9/1982 | Calvin et al. |
| 4,348,487 A | 9/1982 | Goldstein et al. |
| 4,353,713 A | 10/1982 | Cheng |
| 4,365,975 A | 12/1982 | Williams et al. |
| 4,372,755 A | 2/1983 | Tolman et al. |
| 4,375,362 A | 3/1983 | Moss |
| 4,385,905 A | 5/1983 | Tucker |
| 4,397,656 A | 8/1983 | Ketkar |
| 4,400,182 A | 8/1983 | Davies et al. |
| 4,407,206 A | 10/1983 | Bartok et al. |
| 4,428,535 A | 1/1984 | Venetucci |
| 4,432,773 A | 2/1984 | Euker, Jr. et al. |
| 4,433,065 A | 2/1984 | Van Der Burgt et al. |
| 4,436,028 A | 3/1984 | Wilder |
| 4,436,531 A | 3/1984 | Estabrook et al. |
| 4,439,210 A | 3/1984 | Lancet |
| 4,443,415 A | 4/1984 | Queneau et al. |
| 4,444,568 A | 4/1984 | Beisswenger et al. |
| 4,459,138 A | 7/1984 | Soung |
| 4,462,814 A | 7/1984 | Holmes et al. |
| 4,466,828 A | 8/1984 | Tamai et al. |
| 4,468,231 A | 8/1984 | Bartok et al. |
| 4,478,425 A | 10/1984 | Benko |
| 4,478,725 A | 10/1984 | Velling et al. |
| 4,482,529 A | 11/1984 | Chen et al. |
| 4,491,609 A | 1/1985 | Degel et al. |
| 4,497,784 A | 2/1985 | Diaz |
| 4,500,323 A | 2/1985 | Siegfried et al. |
| 4,505,881 A | 3/1985 | Diaz |
| 4,508,544 A | 4/1985 | Moss |
| 4,508,693 A | 4/1985 | Diaz |
| 4,515,604 A | 5/1985 | Eisenlohr et al. |
| 4,515,764 A | 5/1985 | Diaz |
| 4,524,050 A | 6/1985 | Chen et al. |
| 4,540,681 A | 9/1985 | Kustes et al. |
| 4,541,841 A | 9/1985 | Reinhardt |
| 4,551,155 A | 11/1985 | Wood et al. |
| 4,558,027 A | 12/1985 | McKee et al. |
| 4,572,826 A | 2/1986 | Moore |
| 4,594,140 A | 6/1986 | Cheng |
| 4,597,775 A | 7/1986 | Billimoria et al. |
| 4,597,776 A | 7/1986 | Ullman et al. |
| 4,604,105 A | 8/1986 | Aquino et al. |
| 4,609,388 A | 9/1986 | Adler et al. |
| 4,609,456 A | 9/1986 | Deschamps et al. |
| 4,617,027 A | 10/1986 | Lang |
| 4,619,864 A | 10/1986 | Hendrix et al. |
| 4,620,421 A | 11/1986 | Brown et al. |
| 4,661,237 A | 4/1987 | Kimura et al. |
| 4,668,428 A | 5/1987 | Najjar |
| 4,668,429 A | 5/1987 | Najjar |
| 4,675,035 A | 6/1987 | Apffel |
| 4,678,480 A | 7/1987 | Heinrich et al. |
| 4,682,986 A | 7/1987 | Lee et al. |
| 4,690,814 A | 9/1987 | Velenyi et al. |
| 4,696,678 A | 9/1987 | Koyama et al. |
| 4,699,632 A | 10/1987 | Babu et al. |
| 4,704,136 A | 11/1987 | Weston et al. |
| 4,720,289 A | 1/1988 | Vaugh et al. |

(56) References Cited

U.S. PATENT DOCUMENTS

| | | |
|---|---|---|
| 4,747,938 A | 5/1988 | Khan |
| 4,781,731 A | 11/1988 | Schlinger |
| 4,803,061 A | 2/1989 | Najjar et al. |
| 4,808,194 A | 2/1989 | Najjar et al. |
| 4,810,475 A | 3/1989 | Chu et al. |
| 4,822,935 A | 4/1989 | Scott |
| 4,848,983 A | 7/1989 | Tomita et al. |
| 4,854,944 A | 8/1989 | Strong |
| 4,861,346 A | 8/1989 | Najjar et al. |
| 4,861,360 A | 8/1989 | Apffel |
| 4,872,886 A | 10/1989 | Henley et al. |
| 4,876,080 A | 10/1989 | Paulson |
| 4,892,567 A | 1/1990 | Yan |
| 4,960,450 A | 10/1990 | Schwarz et al. |
| 4,995,193 A | 2/1991 | Soga et al. |
| 5,017,282 A | 5/1991 | Delbianco et al. |
| 5,055,181 A | 10/1991 | Maa et al. |
| 5,057,294 A | 10/1991 | Sheth et al. |
| 5,059,406 A | 10/1991 | Sheth et al. |
| 5,074,357 A | 12/1991 | Haines |
| 5,093,094 A | 3/1992 | Van Kleeck et al. |
| 5,094,737 A | 3/1992 | Bearden, Jr. et al. |
| 5,132,007 A | 7/1992 | Meyer et al. |
| 5,223,173 A | 6/1993 | Jeffrey |
| 5,225,044 A | 7/1993 | Breu |
| 5,236,557 A | 8/1993 | Muller et al. |
| 5,250,083 A | 10/1993 | Wolfenbarger et al. |
| 5,277,884 A | 1/1994 | Shinnar et al. |
| 5,388,645 A | 2/1995 | Puri et al. |
| 5,388,650 A | 2/1995 | Michael |
| 5,435,940 A | 7/1995 | Doering et al. |
| 5,536,893 A | 7/1996 | Gudmundsson |
| 5,566,755 A | 10/1996 | Seidle et al. |
| 5,616,154 A | 4/1997 | Elliott et al. |
| 5,630,854 A | 5/1997 | Sealock, Jr. et al. |
| 5,641,327 A | 6/1997 | Leas |
| 5,660,807 A | 8/1997 | Forg et al. |
| 5,669,960 A | 9/1997 | Couche |
| 5,670,122 A | 9/1997 | Zamansky et al. |
| 5,720,785 A | 2/1998 | Baker |
| 5,733,515 A | 3/1998 | Doughty et al. |
| 5,769,165 A | 6/1998 | Bross et al. |
| 5,776,212 A | 7/1998 | Leas |
| 5,788,724 A | 8/1998 | Carugati et al. |
| 5,855,631 A | 1/1999 | Leas |
| 5,865,898 A | 2/1999 | Holtzapple et al. |
| 5,968,465 A | 10/1999 | Koveal et al. |
| 6,013,158 A | 1/2000 | Wootten |
| 6,015,104 A | 1/2000 | Rich, Jr. |
| 6,028,234 A | 2/2000 | Heinemann et al. |
| 6,032,737 A | 3/2000 | Brady et al. |
| 6,090,356 A | 7/2000 | Jahnke et al. |
| 6,119,778 A | 9/2000 | Seidle et al. |
| 6,132,478 A | 10/2000 | Tsurui et al. |
| 6,180,843 B1 | 1/2001 | Heinemann et al. |
| 6,187,465 B1 | 2/2001 | Galloway |
| 6,379,645 B1 | 4/2002 | Bucci et al. |
| 6,389,820 B1 | 5/2002 | Rogers et al. |
| 6,419,888 B1 | 7/2002 | Wyckoff |
| 6,506,349 B1 | 1/2003 | Khanmamedov |
| 6,506,361 B1 | 1/2003 | Machado et al. |
| 6,602,326 B2 | 8/2003 | Lee et al. |
| 6,641,625 B1 | 11/2003 | Clawson et al. |
| 6,653,516 B1 | 11/2003 | Yoshikawa et al. |
| 6,692,711 B1 | 2/2004 | Alexion et al. |
| 6,790,430 B1 | 9/2004 | Lackner et al. |
| 6,797,253 B2 | 9/2004 | Lyon |
| 6,808,543 B2 | 10/2004 | Paisley |
| 6,830,597 B1 | 12/2004 | Green |
| 6,855,852 B1 | 2/2005 | Jackson et al. |
| 6,878,358 B2 | 4/2005 | Vosteen et al. |
| 6,894,183 B2 | 5/2005 | Choudhary et al. |
| 6,955,595 B2 | 10/2005 | Kim |
| 6,955,695 B2 | 10/2005 | Nahas |
| 6,969,494 B2 | 11/2005 | Herbst |
| 7,074,373 B1 | 7/2006 | Warren et al. |
| 7,077,202 B2 | 7/2006 | Shaw et al. |
| 7,100,692 B2 | 9/2006 | Parsley et al. |
| 7,118,720 B1 | 10/2006 | Mendelsohn et al. |
| 7,132,183 B2 | 11/2006 | Galloway |
| 7,168,488 B2 | 1/2007 | Olsvik et al. |
| 7,205,448 B2 | 4/2007 | Gajda et al. |
| 7,220,502 B2 | 5/2007 | Galloway |
| 7,299,868 B2 | 11/2007 | Zapadinski |
| 7,309,383 B2 | 12/2007 | Beech, Jr. et al. |
| 7,481,275 B2 | 1/2009 | Olsvik et al. |
| 7,666,383 B2 | 2/2010 | Green |
| 7,677,309 B2 | 3/2010 | Shaw et al. |
| 7,758,663 B2 | 7/2010 | Rabovitser et al. |
| 7,897,126 B2 | 3/2011 | Rappas et al. |
| 7,901,644 B2 | 3/2011 | Rappas et al. |
| 7,922,782 B2 | 4/2011 | Sheth |
| 7,926,750 B2 | 4/2011 | Hauserman |
| 7,976,593 B2 | 7/2011 | Graham |
| 8,114,176 B2 | 2/2012 | Nahas |
| 8,114,177 B2 | 2/2012 | Hippo et al. |
| 8,123,827 B2 | 2/2012 | Robinson |
| 8,163,048 B2 | 4/2012 | Rappas et al. |
| 8,192,716 B2 | 6/2012 | Raman et al. |
| 8,202,913 B2 | 6/2012 | Robinson et al. |
| 8,268,899 B2 | 9/2012 | Robinson et al. |
| 8,286,901 B2 | 10/2012 | Rappas et al. |
| 8,297,542 B2 | 10/2012 | Rappas et al. |
| 8,328,890 B2 | 12/2012 | Reiling et al. |
| 8,349,037 B2 | 1/2013 | Steiner et al. |
| 8,349,039 B2 | 1/2013 | Robinson |
| 8,361,428 B2 | 1/2013 | Raman et al. |
| 8,366,795 B2 | 2/2013 | Raman et al. |
| 8,479,833 B2 | 7/2013 | Raman |
| 8,479,834 B2 | 7/2013 | Preston |
| 8,502,007 B2 | 8/2013 | Hippo et al. |
| 2002/0036086 A1 | 3/2002 | Minkkinen et al. |
| 2003/0070808 A1 | 4/2003 | Allison |
| 2003/0131582 A1 | 7/2003 | Anderson et al. |
| 2003/0167691 A1 | 9/2003 | Nahas |
| 2004/0020123 A1 | 2/2004 | Kimura et al. |
| 2004/0023086 A1 | 2/2004 | Su et al. |
| 2004/0123601 A1 | 7/2004 | Fan |
| 2004/0180971 A1 | 9/2004 | Inoue et al. |
| 2004/0256116 A1 | 12/2004 | Olsvik et al. |
| 2005/0107648 A1 | 5/2005 | Kimura et al. |
| 2005/0137442 A1 | 6/2005 | Gajda et al. |
| 2005/0192362 A1 | 9/2005 | Rodriguez et al. |
| 2005/0287056 A1 | 12/2005 | Baker et al. |
| 2005/0288537 A1 | 12/2005 | Maund et al. |
| 2006/0149423 A1 | 7/2006 | Barnicki et al. |
| 2006/0228290 A1 | 10/2006 | Green |
| 2006/0231252 A1 | 10/2006 | Shaw et al. |
| 2006/0265953 A1 | 11/2006 | Hobbs |
| 2006/0272813 A1 | 12/2006 | Olsvik et al. |
| 2007/0000177 A1 | 1/2007 | Hippo et al. |
| 2007/0051043 A1 | 3/2007 | Schingnitz |
| 2007/0083072 A1 | 4/2007 | Nahas |
| 2007/0180990 A1 | 8/2007 | Downs et al. |
| 2007/0186472 A1 | 8/2007 | Rabovister et al. |
| 2007/0220810 A1 | 9/2007 | Leveson et al. |
| 2007/0227729 A1 | 10/2007 | Zubrin et al. |
| 2007/0237696 A1 | 10/2007 | Payton |
| 2007/0277437 A1 | 12/2007 | Sheth |
| 2007/0282018 A1 | 12/2007 | Jenkins |
| 2008/0141591 A1 | 6/2008 | Kohl |
| 2008/0289822 A1 | 11/2008 | Betzer Tsilevich |
| 2009/0012188 A1 | 1/2009 | Rojey et al. |
| 2009/0048476 A1 | 2/2009 | Rappas et al. |
| 2009/0090055 A1 | 4/2009 | Ohtsuka |
| 2009/0090056 A1 | 4/2009 | Ohtsuka |
| 2009/0165361 A1 | 7/2009 | Rappas et al. |
| 2009/0165376 A1 | 7/2009 | Lau et al. |
| 2009/0165379 A1 | 7/2009 | Rappas |
| 2009/0165380 A1 | 7/2009 | Lau et al. |
| 2009/0165381 A1 | 7/2009 | Robinson |
| 2009/0165382 A1 | 7/2009 | Rappas et al. |
| 2009/0165383 A1 | 7/2009 | Rappas et al. |
| 2009/0165384 A1 | 7/2009 | Lau et al. |

(56) References Cited

U.S. PATENT DOCUMENTS

| | | | |
|---|---|---|---|
| 2009/0166588 A1 | 7/2009 | Spitz et al. | |
| 2009/0169448 A1 | 7/2009 | Rappas et al. | |
| 2009/0169449 A1 | 7/2009 | Rappas et al. | |
| 2009/0170968 A1 | 7/2009 | Nahas et al. | |
| 2009/0173079 A1 | 7/2009 | Wallace et al. | |
| 2009/0217575 A1 | 9/2009 | Raman et al. | |
| 2009/0217582 A1 | 9/2009 | May et al. | |
| 2009/0217584 A1 | 9/2009 | Raman et al. | |
| 2009/0217585 A1 | 9/2009 | Raman et al. | |
| 2009/0217586 A1 | 9/2009 | Rappas et al. | |
| 2009/0217587 A1 | 9/2009 | Raman et al. | |
| 2009/0217588 A1 | 9/2009 | Hippo et al. | |
| 2009/0217589 A1 | 9/2009 | Robinson | |
| 2009/0217590 A1 | 9/2009 | Rappas et al. | |
| 2009/0218424 A1 | 9/2009 | Hauserman | |
| 2009/0220406 A1 | 9/2009 | Rahman | |
| 2009/0229182 A1 | 9/2009 | Raman et al. | |
| 2009/0235585 A1 | 9/2009 | Neels et al. | |
| 2009/0236093 A1 | 9/2009 | Zubrin et al. | |
| 2009/0246120 A1 | 10/2009 | Raman et al. | |
| 2009/0259080 A1 | 10/2009 | Raman et al. | |
| 2009/0260287 A1 | 10/2009 | Lau | |
| 2009/0305093 A1 | 12/2009 | Biollaz et al. | |
| 2009/0324458 A1 | 12/2009 | Robinson et al. | |
| 2009/0324459 A1 | 12/2009 | Robinson et al. | |
| 2009/0324460 A1 | 12/2009 | Robinson et al. | |
| 2009/0324461 A1 | 12/2009 | Robinson et al. | |
| 2009/0324462 A1 | 12/2009 | Robinson et al. | |
| 2010/0018113 A1 | 1/2010 | Bohlig et al. | |
| 2010/0050654 A1 | 3/2010 | Chiu et al. | |
| 2010/0071235 A1 | 3/2010 | Pan et al. | |
| 2010/0071262 A1 | 3/2010 | Robinson et al. | |
| 2010/0076235 A1 | 3/2010 | Reiling et al. | |
| 2010/0120926 A1 | 5/2010 | Robinson et al. | |
| 2010/0121125 A1 | 5/2010 | Hippo et al. | |
| 2010/0159352 A1 | 6/2010 | Gelin et al. | |
| 2010/0168494 A1 | 7/2010 | Rappas et al. | |
| 2010/0168495 A1 | 7/2010 | Rappas et al. | |
| 2010/0179232 A1* | 7/2010 | Robinson et al. | 518/703 |
| 2010/0287835 A1 | 11/2010 | Reiling et al. | |
| 2010/0287836 A1 | 11/2010 | Robinson et al. | |
| 2010/0292350 A1 | 11/2010 | Robinson et al. | |
| 2011/0031439 A1 | 2/2011 | Sirdeshpande et al. | |
| 2011/0062012 A1 | 3/2011 | Robinson | |
| 2011/0062721 A1 | 3/2011 | Sirdeshpande et al. | |
| 2011/0062722 A1 | 3/2011 | Sirdeshpande et al. | |
| 2011/0064648 A1 | 3/2011 | Preston et al. | |
| 2011/0088896 A1 | 4/2011 | Preston | |
| 2011/0088897 A1 | 4/2011 | Raman | |
| 2011/0146978 A1 | 6/2011 | Perlman | |
| 2011/0146979 A1 | 6/2011 | Wallace | |
| 2011/0207002 A1 | 8/2011 | Powell et al. | |
| 2011/0217602 A1 | 9/2011 | Sirdeshpande | |
| 2011/0262323 A1 | 10/2011 | Rappas et al. | |
| 2011/0294905 A1 | 12/2011 | Robinson et al. | |
| 2012/0046510 A1 | 2/2012 | Sirdeshpande | |
| 2012/0060417 A1 | 3/2012 | Raman et al. | |
| 2012/0102836 A1 | 5/2012 | Raman et al. | |
| 2012/0102837 A1 | 5/2012 | Raman et al. | |
| 2013/0042824 A1 | 2/2013 | Sirdeshpande | |
| 2013/0046124 A1 | 2/2013 | Sirdeshpande | |
| 2013/0172640 A1 | 7/2013 | Robinson et al. | |

FOREIGN PATENT DOCUMENTS

| | | |
|---|---|---|
| CA | 1041553 | 10/1978 |
| CA | 1106178 | 8/1981 |
| CA | 1 125 026 | 6/1982 |
| CA | 1187702 | 6/1985 |
| CA | 1282243 | 4/1991 |
| CA | 1299589 | 4/1992 |
| CA | 1332108 | 9/1994 |
| CA | 2673121 | 6/2008 |
| CA | 2713642 | 7/2009 |
| CN | 1477090 | 2/2004 |
| CN | 101555420 | 10/2009 |
| DE | 2 210 891 | 3/1972 |
| DE | 2210891 | 9/1972 |
| DE | 2852710 | 6/1980 |
| DE | 3422202 | 12/1985 |
| DE | 100610607 | 6/2002 |
| EA | 819 | 4/2000 |
| EP | 0024792 | 3/1981 |
| EP | 0 067 580 | 12/1982 |
| EP | 0102828 A2 * | 8/1983 |
| EP | 102828 | 3/1984 |
| EP | 0 138 463 | 4/1985 |
| EP | 0 225 146 | 6/1987 |
| EP | 0 259 927 | 3/1988 |
| EP | 0473153 | 3/1992 |
| EP | 0 723 930 | 7/1996 |
| EP | 1 001 002 | 5/2000 |
| EP | 1004746 | 5/2000 |
| EP | 1136542 | 9/2001 |
| EP | 1 207 132 | 5/2002 |
| EP | 1 741 673 | 6/2006 |
| EP | 1768207 | 3/2007 |
| EP | 2058471 | 5/2009 |
| FR | 797 089 | 4/1936 |
| FR | 2 478 615 | 9/1981 |
| FR | 2906879 | 4/2008 |
| GB | 593910 | 10/1947 |
| GB | 640907 | 8/1950 |
| GB | 676615 | 7/1952 |
| GB | 701 131 | 12/1953 |
| GB | 760627 | 11/1956 |
| GB | 798741 | 7/1958 |
| GB | 820 257 | 9/1959 |
| GB | 996327 | 6/1965 |
| GB | 1033764 | 6/1966 |
| GB | 1448562 | 9/1976 |
| GB | 1453081 | 10/1976 |
| GB | 1467219 | 3/1977 |
| GB | 1467995 | 3/1977 |
| GB | 1 599 932 | 7/1977 |
| GB | 1560873 | 2/1980 |
| GB | 2078251 | 1/1982 |
| GB | 2154600 | 9/1985 |
| GB | 2455864 | 6/2009 |
| JP | 53-94305 | 8/1978 |
| JP | 53-111302 | 9/1978 |
| JP | 54020003 | 2/1979 |
| JP | 54-150402 | 11/1979 |
| JP | 55-12181 | 1/1980 |
| JP | 56-145982 | 11/1981 |
| JP | 56157493 | 12/1981 |
| JP | 60-35092 | 2/1985 |
| JP | 60-77938 | 5/1985 |
| JP | 62241991 | 10/1987 |
| JP | 62 257985 | 11/1987 |
| JP | 03-115491 | 5/1991 |
| JP | 2000290659 | 10/2000 |
| JP | 2000290670 | 10/2000 |
| JP | 2002105467 | 4/2002 |
| JP | 2004292200 | 10/2004 |
| JP | 2004298818 | 10/2004 |
| JP | 2006 169476 A | 6/2006 |
| WO | 00/18681 | 4/2000 |
| WO | WO 00/43468 | 7/2000 |
| WO | WO 02/40768 | 5/2002 |
| WO | WO 02/079355 | 10/2002 |
| WO | 02/103157 | 12/2002 |
| WO | 03/018958 | 3/2003 |
| WO | WO 03/033624 | 4/2003 |
| WO | 2004/055323 | 7/2004 |
| WO | WO 2004/072210 | 8/2004 |
| WO | WO 2006/031011 | 3/2006 |
| WO | WO 2007/005284 | 1/2007 |
| WO | WO 2007/047210 | 4/2007 |
| WO | 2007/068682 | 6/2007 |
| WO | 2007/077137 | 7/2007 |
| WO | 2007/077138 | 7/2007 |
| WO | 2007/083072 | 7/2007 |

(56) References Cited

FOREIGN PATENT DOCUMENTS

| | | |
|---|---|---|
| WO | WO 2007/076363 | 7/2007 |
| WO | WO 2007/128370 | 11/2007 |
| WO | 2007/143376 | 12/2007 |
| WO | WO 2007/143376 | 12/2007 |
| WO | 2008/058636 | 5/2008 |
| WO | WO 2008/073889 | 6/2008 |
| WO | 2008/087154 | 7/2008 |
| WO | 2009/018053 | 2/2009 |
| WO | WO 2009/018053 | 2/2009 |
| WO | WO 2009/048723 | 4/2009 |
| WO | WO 2009/048724 | 4/2009 |
| WO | WO 2009/086361 | 7/2009 |
| WO | WO 2009/086362 | 7/2009 |
| WO | WO 2009/086363 | 7/2009 |
| WO | WO 2009/086366 | 7/2009 |
| WO | WO 2009/086367 | 7/2009 |
| WO | WO 2009/086370 | 7/2009 |
| WO | WO 2009/086372 | 7/2009 |
| WO | WO 2009/086374 | 7/2009 |
| WO | WO 2009/086377 | 7/2009 |
| WO | WO 2009/086383 | 7/2009 |
| WO | WO 2009/086407 | 7/2009 |
| WO | WO 2009/086408 | 7/2009 |
| WO | WO 2009/111330 | 9/2009 |
| WO | WO 2009/111331 | 9/2009 |
| WO | WO 2009/111332 | 9/2009 |
| WO | WO 2009/111335 | 9/2009 |
| WO | WO 2009/111342 | 9/2009 |
| WO | WO 2009/111345 | 9/2009 |
| WO | WO 2009/124017 | 10/2009 |
| WO | WO 2009/124019 | 10/2009 |
| WO | WO 2009/158576 | 12/2009 |
| WO | WO 2009/158579 | 12/2009 |
| WO | WO 2009/158580 | 12/2009 |
| WO | WO 2009/158582 | 12/2009 |
| WO | WO 2009/158583 | 12/2009 |
| WO | WO 2010/033846 | 3/2010 |
| WO | WO 2010/033848 | 3/2010 |
| WO | WO 2010/033850 | 3/2010 |
| WO | WO 2010/033852 | 3/2010 |
| WO | WO 2010/048493 | 4/2010 |
| WO | WO 2010/078297 | 7/2010 |
| WO | WO 2010/078298 | 7/2010 |
| WO | 2010/132549 | 11/2010 |
| WO | WO 2010/132551 | 11/2010 |
| WO | 2011/017630 | 2/2011 |
| WO | 2011/029278 | 3/2011 |
| WO | 2011/029282 | 3/2011 |
| WO | 2011/029283 | 3/2011 |
| WO | 2011/029284 | 3/2011 |
| WO | 2011/029285 | 3/2011 |
| WO | 2011/034888 | 3/2011 |
| WO | 2011/034889 | 3/2011 |
| WO | 2011/034891 | 3/2011 |
| WO | WO 2011/034890 | 3/2011 |
| WO | 2011/049858 | 4/2011 |
| WO | 2011/049861 | 4/2011 |
| WO | 2011/063608 | 6/2011 |
| WO | WO 2011076994 A1 * | 6/2011 |
| WO | 2011/084580 | 7/2011 |
| WO | 2011/084581 | 7/2011 |
| WO | 2011/106285 | 9/2011 |
| WO | 2011/139694 | 11/2011 |
| WO | 2011/150217 | 12/2011 |
| WO | WO 2012/024369 | 2/2012 |
| WO | 2012/033997 | 3/2012 |
| WO | 2012/061235 | 5/2012 |
| WO | 2012/061238 | 5/2012 |
| WO | 2012/116003 | 8/2012 |
| WO | 2012/145497 | 10/2012 |
| WO | 2012/166879 | 12/2012 |
| WO | 2013/025808 | 2/2013 |
| WO | 2013/025812 | 2/2013 |
| WO | 2013/052553 | 4/2013 |

OTHER PUBLICATIONS

U.S. Appl. No. 12/778,548, filed May 12, 2010, Robinson, et al.
U.S. Appl. No. 12/778,552, filed May 12, 2010, Robinson, et al.
Adsorption, http://en.wikipedia.org/wiki/Adsorption, pp. 1-8 (Oct. 17, 2007).
Amine gas treating, http://en.wikipedia.org/wiki/Acid_gas_removal, pp. 1-4 (Oct. 21, 2007).
Coal, http://en.wikipedia.org/wiki/Coal_gasification, pp. 1-8 (Oct. 29, 2007).
Coal Data: A Reference, Energy Information Administration, Office of Coal, Nuclear, Electric, and Alternate Fuels U.S. Department of Energy, DOE/EIA-0064(93), Feb. 1995.
Deepak Tandon, Dissertation Approval, "Low Temperature and Elevated Pressure Steam Gasification of Illinois Coal", Jun. 13, 1996.
Demibras, "Demineralization of Agricultural Residues by Water Leaching", *Energy Sources*, vol. 25, pp. 679-687, (2003).
Fluidized Bed Gasifiers, http://www.energyproducts.com/fluidized_bed_gasifiers.htm, Oct. 2007, pp. 1-5.
Gas separation, http://en.wikipedia.org/wiki/Gas_separation, pp. 1-2 (Feb. 24, 2007).
Gasification, http://en.wikipedia.org/wiki/Gasification, pp. 1-6 (Oct. 29, 2007).
Gallagher Jr., et al., "Catalytic Coal Gasification for SNG Manufacture", *Energy Research*, vol. 4, pp. 137-147, (1980).
Heinemann, et al., "Fundamental and Exploratory Studies of Catalytic Steam Gasification of Carbonaceous Materials", Final Report Fiscal Years 1985-1994.
Jensen, et al. Removal of K and Cl by leaching of straw char, *Biomass and Bioenergy*, vol. 20, pp. 447-457, (2001).
Mengjie, et al., "A potential renewable energy resource development and utilization of biomass energy", http://www.fao.org.docrep/T4470E/t4470e0n.htm, pp. 1-8 1994.
Meyers, et al. Fly Ash as A Construction Material for Highways, A Manual. Federal Highway Administration, Report No. FHWA-IP-76-16, Washington, DC, 1976.
Moulton, Lyle K. "Bottom Ash and Boiler Slag", *Proceedings of the Third International Ash Utilization Symposium*, U.S. Bureau of Mines, Information Circular No. 8640, Washington, DC, 1973.
Natural gas processing, http://en.wikipedia.org/wiki/Natural_gas_processing, pp. 1-4 (Oct. 22, 2007).
Natural Gas Processing: The Crucial Link Between Natural Gas Production and Its Transportation to Market. Energy Information Administration, Office of Oil and Gas; pp. 1-11, (2006).
Prins, et al., "Exergetic optimisation of a production process of Fischer-Tropsch fuels from biomass", *Fuel Processing Technology*, vol. 86, pp. 375-389, (2004).
Reboiler, http://en.wikipedia.org/wiki/Reboiler, pp. 1-4 (Nov. 11, 2007).
What is XPS?, http://www.nuance.northwestern.edu/Keckll/xps1.asp, 2006, pp. 1-2 (2006).
2.3 Types of gasifiers, http://www.fao.org/docrep/t0512e/T0512e0a.htm, pp. 1-6 (1986).
2.4 Gasification fuels, http://www.fao.org/docrep/t0512e/T0512e0b.htm, pp. 1-8 (1986).
2.5 Design of downdraught gasifiers, http://www.fao.org/docrep/t0512e/T0512e0c.htm#TopOfPage, pp. 1-8 (1986).
2.6 Gas cleaning and cooling, http://www.fao.org/docrep/t0512e0d.htm#TopOFPage, pp. 1-3 (1986).
A.G. Collot et al., "Co-pyrolysis and co-gasification of coal and biomass in bench-scale fixed-bed and fluidized bed reactors", (1999) Fuel 78, pp. 667-679.
Wenkui Zhu et al., "Catalytic gasification of char from co-pyrolysis of coal and biomass", (2008) Fuel Processing Technology, vol. 89, pp. 890-896.
Chiesa P. et al., "Co-Production of hydrogen, electricity and C02 from coal with commercially ready technology. Part A: Performance and emissions", (2005) International Journal of Hydrogen Energy, vol. 30, No. 7, pp. 747-767.
Chiaramonte et al, "Upgrade Coke by Gasification", (1982) Hydrocarbon Processing, vol. 61 (9), pp. 255-257 (Abstract only).

(56) References Cited

OTHER PUBLICATIONS

Asami, K., et al., "Highly Active Iron Catalysts from Ferric Chloride or the Steam Gasification of Brown Coal," ind. Eng. Chem. Res., vol. 32, No. 8, 1993, pp. 1631-1636.

Berger, R., et al., "High Temperature $CO_2$-Absorption: A Process Offering New Prospects in Fuel Chemistry," The Fifth International Symposium on Coal Combustion, Nov. 2003, Nanjing, China, pp. 547-549.

Brown et al., "Biomass-Derived Hydrogen From A Thermally Ballasted Gasifier," Aug. 2005.

Brown et al., "Biomass-Derived Hydrogen From A Thermally Ballasted Gasifier," DOE Hydrogen Program Contractors' Review Metting, Center for Sustainable Environmental Technologies, Iowa State University, May 21, 2003.

Cohen, S.J., Project Manager, "Large Pilot Plant Alternatives for Scaleup of the Catalytic Coal Gasification Process," FE-2480-20, U.S. Dept. of Energy, Contract No. EX-76-C-01-2480, 1979.

Euker, Jr., C.A., Reitz, R.A., Program Managers, "Exxon Catalytic Coal-Gasification-Process Development Program," Exxon Research & Engineering Company, FE-2777-31, U.S. Dept. of Energy, Contract No. ET-78-C-01-2777, 1981.

Kalina, T., Nahas, N.C., Project Managers, "Exxon Catalaytic Coal Gasification Process Predevelopment Program," Exxon Research & Engineering Company, FE-2369-24, U.S. Dept. of Energy, Contract No. E(49-18)-2369, 1978.

Nahas, N.C., "Exxon Catalytic Coal Gasification Process—Fundamentals to Flowsheets," Fuel, vol. 62, No. 2, 1983, pp. 239-241.

Ohtsuka, Y. et al., "Highly Active Catalysts from Inexpensive Raw Materials for Coal Gasification," Catalysis Today, vol. 39, 1997, pp. 111-125.

Ohtsuka, Yasuo et al, "Steam Gasification of Low-Rank Coals with a Chlorine-Free Iron Catalyst from Ferric Chloride," Ind. Eng. Chem. Res., vol. 30, No. 8, 1991, pp. 1921-1926.

Ohtsuka, Yasuo et al., "Calcium Catalysed Steam Gasification of Yalourn Brown Coal," Fuel, vol. 65, 1986, pp. 1653-1657.

Ohtsuka, Yasuo, et al, "Iron-Catalyzed Gasification of Brown Coal at Low Temperatures," Energy & Fuels, vol. 1, No. 1, 1987, pp. 32-36.

Ohtsuka, Yasuo, et al., "Ion-Exchanged Calcium From Calcium Carbonate and Low-Rank Coals: High Catalytic Activity in Steam Gasification," Energy & Fuels 1996, 10, pp. 431-435.

Ohtsuka, Yasuo et al., "Steam Gasification of Coals with Calcium Hydroxide," Energy & Fuels, vol. 9, No. 6, 1995, pp. 1038-1042.

Pereira, P., et al., "Catalytic Steam Gasification of Coals," Energy & Fuels, vol. 6, No. 4, 1992, pp. 407-410.

Ruan Xiang-Quan, et al., "Effects of Catalysis on Gasification of Tatong Coal Char," Fuel, vol. 66, Apr. 1987, pp. 568-571.

Tandon, D., "Low Temperature and Elevated Pressure Steam Gasification of Illinois Coal," College of Engineering in the Graduate School, Southern Illinois university at Carbondale, Jun. 1996.

Hydromethanation Process, GreatPoint Energy, Inc., from World Wide Web <http://greatpointenergy.com/ourtechnology.php.> accessed Sep. 5, 2013.

Sigma-Aldrich "Particle Size Conversion Table" (2004); from World Wide Web <http:/www.sigmaaldrich.com/chemistry/learning-center/technical-library/particle-size-conversion.printerview.html>.

Gerdes, Kristin, et al., "Integrated Gasification Fuel Cell Performance and Cost Assessment," National Energy Technology Laboratory, U.S. Department of Energy, Mar. 27, 2009, pp. 1-26.

Ghosh, S., et al., "Energy Analysis of a Cogeneration Plant Using Coal Gasification and Solid Oxide Fuel Cell," Energy, 2006, vol. 31, No. 2-3, pp. 345-363.

Jeon, S.K., et al., "Characteristics of Steam Hydrogasification of Wood Using A Micro-Batch Reactor," Fuel, 2007, vol. 86, pp. 2817-2823.

Li, Mu, et al., "Design of Highly Efficient Coal-Based Integrated Gasification Fuel Cell Power Plants," Journal of Power Sources, 2010, vol. 195, pp. 5707-5718.

Prins, M.J., et al., "Exergetic Optimisation of a Production Process of Fischer-Tropsch Fuels from Biomass," Fuel Processing Technology, 2005, vol. 86, No. 4, pp. 375-389.

U.S. Appl. No. 13/484,918, filed May 31, 2012.
U.S. Appl. No. 13/402,022, filed Feb. 22, 2012.
U.S. Appl. No. 13/450,995, filed Apr. 19, 2012.

\* cited by examiner

HYDROMETHANATION OF A CARBONACEOUS FEEDSTOCK

CROSS-REFERENCE TO RELATED APPLICATION

This application claims priority under 35 U.S.C. §119 from U.S. Provisional Application Ser. No. 61/544,029 (filed 6 Oct. 2011), the disclosure of which is incorporated by reference herein for all purposes as if fully set forth.

FIELD OF THE INVENTION

The present invention relates generally to processes for hydromethanating a carbonaceous feedstock in a hydromethanation reactor to a methane product stream and a char by-product, and more specifically to removal of the char by-product from the hydromethanation reactor.

BACKGROUND OF THE INVENTION

In view of numerous factors such as higher energy prices and environmental concerns, the production of value-added products (such as pipeline-quality substitute natural gas, hydrogen, methanol, higher hydrocarbons, ammonia and electrical power) from lower-fuel-value carbonaceous feedstocks (such as petroleum coke, resids, asphaltenes, coal and biomass) is receiving renewed attention.

Such lower-fuel-value carbonaceous feedstocks can be gasified at elevated temperatures and pressures to produce a synthesis gas stream that can subsequently be converted to such value-added products.

One advantageous gasification process is hydromethanation, in which the carbonaceous feedstock is converted in a fluidized-bed hydromethanation reactor in the presence of a catalyst source and steam at moderately-elevated temperatures and pressures to directly produce a methane-enriched synthesis gas stream (medium BTU synthesis gas stream) raw product. This is distinct from conventional gasification processes, such as those based on partial combustion/oxidation of a carbon source at highly-elevated temperatures and pressures (thermal gasification, typically non-catalytic), where a syngas (carbon monoxide+hydrogen) is the primary product (little or no methane is directly produced), which can then be further processed to produce methane (via catalytic methanation, see reaction (III) below) or any number of other higher hydrocarbon products.

Hydromethanation processes and the conversion/utilization of the resulting methane-rich synthesis gas stream to produce value-added products are disclosed, for example, in U.S. Pat. No. 3,828,474, U.S. Pat. No. 3,958,957, U.S. Pat. No. 3,998,607, U.S. Pat. No. 4,057,512, U.S. Pat. No. 4,092,125, U.S. Pat. No. 4,094,650, U.S. Pat. No. 4,204,843, U.S. Pat. No. 4,243,639, U.S. Pat. No. 4,468,231, U.S. Pat. No. 4,500,323, U.S. Pat. No. 4,541,841, U.S. Pat. No. 4,551,155, U.S. Pat. No. 4,558,027, U.S. Pat. No. 4,604,105, U.S. Pat. No. 4,617,027, U.S. Pat. No. 4,609,456, U.S. Pat. No. 5,017,282, U.S. Pat. No. 5,055,181, U.S. Pat. No. 6,187,465, U.S. Pat. No. 6,790,430, U.S. Pat. No. 6,894,183, U.S. Pat. No. 6,955,695, US2003/0167691A1, US2006/0265953A1, US2007/000177A1, US2007/083072A1, US2007/0277437A1, US2009/0048476A1, US2009/0090056A1, US2009/0090055A1, US2009/0165383A1, US2009/0166588A1, US2009/0165379A1, US2009/0170968A1, US2009/0165380A1, US2009/0165381A1, US2009/0165361A1, US2009/0165382A1, US2009/0169449A1, US2009/0169448A1, US2009/0165376A1, US2009/0165384A1, US2009/0217582A1, US2009/0220406A1, US2009/0217590A1, US2009/0217586A1, US2009/0217588A1, US2009/0218424A1, US2009/0217589A1, US2009/0217575A1, US2009/0229182A1, US2009/0217587A1, US2009/0246120A1, US2009/0259080A1, US2009/0260287A1, US2009/0324458A1, US2009/0324459A1, US2009/0324460A1, US2009/0324461A1, US2009/0324462A1, US2010/0071235A1, US2010/0071262A1, US2010/0120926A1, US2010/0121125A1, US2010/0168494A1, US2010/0168495A1, US2010/0179232A1, US2010/0287835A1, US2010/0287836A1, US2010/0292350A1, US2011/0031439A1, US2011/0062012A1, US2011/0062721A1, US2011/0062722A1, US2011/0064648A1, US2011/0088896A1, US2011/0088897A1, US2011/0146978A1, US2011/0146979A1, US2011/0207002A1, US2011/0217602A1, WO2011/029278A1, WO2011/029282A1, WO2011/029283A1, WO2011/029284A1, WO2011/029285A1, WO2011/063608A1 and GB1599932. See also Chiaramonte et al, "Upgrade Coke by Gasification", Hydrocarbon Processing, September 1982, pp. 255-257; and Kalina et al, "Exxon Catalytic Coal Gasification Process Predevelopment Program, Final Report", Exxon Research and Engineering Co., Baytown, Tex., FE236924, December 1978.

The hydromethanation of a carbon source typically involves four theoretically separate reactions:

$$\text{Steam carbon: } C+H_2O \rightarrow CO+H_2 \qquad (I)$$

$$\text{Water-gas shift: } CO+H_2O \rightarrow H_2+CO_2 \qquad (II)$$

$$\text{CO Methanation: } CO+3H_2 \rightarrow CH_4+H_2O \qquad (III)$$

$$\text{Hydro-gasification: } 2H_2+C \rightarrow CH_4 \qquad (IV)$$

In the hydromethanation reaction, the first three reactions (I-III) predominate to result in the following overall reaction:

$$2C+2H_2O \rightarrow CH_4+CO_2 \qquad (V).$$

The overall hydromethanation reaction is essentially thermally balanced; however, due to process heat losses and other energy requirements (such as required for evaporation of moisture entering the reactor with the feedstock), some heat must be added to maintain the thermal balance.

The reactions are also essentially syngas (hydrogen and carbon monoxide) balanced (syngas is produced and consumed); therefore, as carbon monoxide and hydrogen are withdrawn with the product gases, carbon monoxide and hydrogen need to be added to the reaction as required to avoid a deficiency.

In order to maintain the net heat of reaction as close to neutral as possible (only slightly exothermic or endothermic), and maintain the syngas balance, a superheated gas stream of steam, carbon monoxide and hydrogen is often fed to the hydromethanation reactor. Frequently, the carbon monoxide and hydrogen streams are recycle streams separated from the product gas, and/or are provided by reforming/partially oxidating a portion of the product methane. See, for example, previously incorporated U.S. Pat. No. 4,094,650, U.S. Pat. No. 6,955,595, US2007/083072A1, US2010/0120926A1, US2010/0287836A1, US2011/0031439A1, US2011/0062722A1 and US2011/0064648A1.

In one variation of the hydromethanation process, required carbon monoxide, hydrogen and heat energy can also at least in part be generated in situ by feeding oxygen into the hydromethanation reactor. See, for example, previously incorporated US2010/0076235A1, US2010/0287835A1 and US2011/0062721A1, as well as commonly-owned US2012/0046510A1, US2012/0060417A1, US2012/0102836A1, US2012/0102837A1, U.S. patent application Ser. No. 13/586,570 (entitled HYDROMETHANATION OF A CARBONACEOUS FEEDSTOCK), which was filed 15 Aug. 2012, and U.S. patent application Ser. No. 13/586,577 (entitled HYDROMETHANATION OF A CARBONACEOUS FEEDSTOCK), which was filed 15 Aug. 2011.

The result is a "direct" methane-enriched raw product gas stream also containing substantial amounts of hydrogen, carbon monoxide and carbon dioxide which can, for example, be directly utilized as a medium BTU energy source, or can be processed to result in a variety of higher-value product streams such as pipeline-quality substitute natural gas, high-purity hydrogen, methanol, ammonia, higher hydrocarbons, carbon dioxide (for enhanced oil recovery and industrial uses) and electrical energy.

A char by-product stream is also produced in addition to the methane-enriched raw product gas stream. The solid char by-product contains unreacted carbon, entrained hydromethanation catalyst and other inorganic components of the carbonaceous feedstock. The by-product char may contain 35 wt % or more carbon depending on the feedstock composition and hydromethanation conditions.

This by-product char is periodically or continuously removed from the hydromethanation reactor, and typically sent to a catalyst recovery and recycle operation to improve economics and commercial viability of the overall process. The nature of catalyst components associated with the char extracted from a hydromethanation reactor and methods for their recovery are disclosed, for example, in previously incorporated US2007/0277437A1, US2009/0165383A1, US2009/0165382A1, US2009/0169449A1 and US2009/0169448A1, as well as commonly-owned US2011/0262323A1 and US2012/0213680A1. Catalyst recycle can be supplemented with makeup catalyst as needed, such as disclosed in previously incorporated US2009/0165384A1.

As the hydromethanation reactor is a pressurized vessel, typically operating at pressures of about 250 psig (about 1825 kPa, absolute) and greater, removal of by-product char from the hydromethanation reactor typically involves the use of a lock-hopper unit, which is a series of pressure-sealed chambers for bringing the removed solids to a pressure appropriate for further processing. The use of a lock-hopper has some disadvantages, including the loss of some product gases which are carried with the removed solids. Other methods for char removal are disclosed, for example, in EP-A-0102828 and CN101555420A.

The hydromethanation reactor also operates at elevated temperature, so the solids coming out of the reactor are at elevated temperature as well. As a result, the solids at some point need to be cooled to an appropriate temperature for further catalyst processing. While this cooling is an opportunity for heat recovery in the process (e.g., via steam generation), it is a point of inefficiency, and also requires additional equipment (e.g., a char cooler) and capital expense.

It would, therefore, be desirable to find a way to more efficiently remove the char by-product from the hydromethanation reactor.

SUMMARY OF THE INVENTION

In one aspect, the invention provides a process for generating a methane-enriched raw product gas stream and a gas-stripped char stream from a non-gaseous carbonaceous material, the process comprising the steps of:

(a) preparing a carbonaceous feedstock from the non-gaseous carbonaceous material;

(b) introducing the carbonaceous feedstock and a hydromethanation catalyst into a hydromethanation reactor, wherein the hydromethanation reactor comprises a char-withdrawal standpipe having a withdrawal end extending into the hydromethanation reactor and a discharge end extending out of the hydromethanation reactor;

(c) reacting the carbonaceous feedstock in the hydromethanation reactor in the presence of carbon monoxide, hydrogen, steam and hydromethanation catalyst, and at an operating temperature of at least about 1000° F. (at least about 538° C.) and an operating pressure of at least about 250 psig (about 1825 kPa) to produce a methane-enriched raw product gas and a solid by-product char;

(d) withdrawing a stream of the methane-enriched raw product gas from the hydromethanation reactor as the methane-enriched raw product gas stream, wherein the methane-enriched raw product gas stream comprises methane, carbon monoxide, hydrogen, carbon dioxide, hydrogen sulfide, steam and heat energy;

(e) withdrawing a stream of the solid by-product char from the hydromethanation reactor via the withdrawal end of the char-withdrawal standpipe, wherein the stream of solid by-product char flows from the withdrawal end to the discharge end of the char-withdrawal standpipe, and wherein the withdrawn solid by-product char comprises an entrained gas;

(f) feeding a stripping gas into the char-withdrawal standpipe such that the stripping gas flows in a countercurrent direction to the flow of the stream of by-product char within the char-withdrawal standpipe to generate (1) a stripped gas stream enriched in the entrained gas and (2) a gas-stripped char stream depleted in the entrained gas;

(g) feeding the stripped gas stream into the hydromethanation reactor via the char-withdrawal standpipe;

(h) feeding the gas-stripped char stream to a screw discharge unit in communication with the discharge end of the char-withdrawal standpipe;

(i) discharging the gas-stripped char stream from the screw discharge unit at a superatmospheric pressure.

The process in accordance with the present invention is useful, for example, for more efficiently producing higher-value products and by-products from various carbonaceous materials at a reduced capital and operating intensity, and greater overall process efficiency.

These and other embodiments, features and advantages of the present invention will be more readily understood by those of ordinary skill in the art from a reading of the following detailed description.

DETAILED DESCRIPTION

Figure 1:
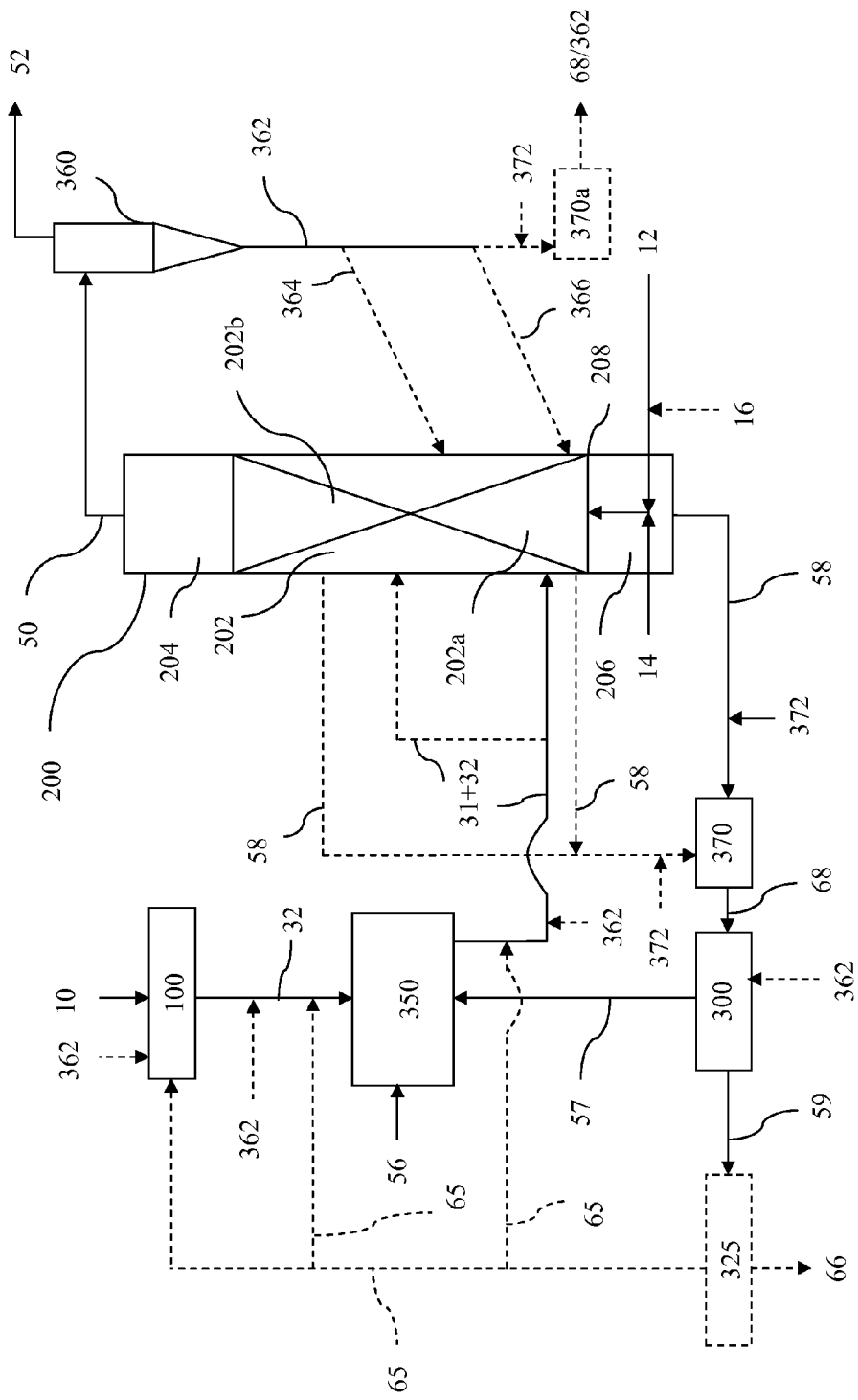
FIG. 1 is a general diagram of an embodiment of the process for generating a methane-enriched raw product gas stream and a gas-stripped char stream from a non-gaseous carbonaceous material in accordance with the present invention.

The present invention relates to processes for converting a non-gaseous carbonaceous material ultimately into one or more value-added gaseous products. Further details are provided below.

In the context of the present description, all publications, patent applications, patents and other references mentioned herein, if not otherwise indicated, are explicitly incorporated by reference herein in their entirety for all purposes as if fully set forth.

Unless otherwise defined, all technical and scientific terms used herein have the same meaning as commonly understood by one of ordinary skill in the art to which this disclosure belongs. In case of conflict, the present specification, including definitions, will control.

Except where expressly noted, trademarks are shown in upper case.

Unless stated otherwise, all percentages, parts, ratios, etc., are by weight.

Unless stated otherwise, pressures expressed in psi units are gauge, and pressures expressed in kPa units are absolute. Pressure differences, however, are expressed as absolute (for example, pressure 1 is 25 psi higher than pressure 2).

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

When the term "about" is used in describing a value or an end-point of a range, the disclosure should be understood to include the specific value or end-point referred to.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus.

Further, unless expressly stated to the contrary, "or" and "and/or" refers to an inclusive and not to an exclusive. For example, a condition A or B, or A and/or B, is satisfied by any one of the following: A is true (or present) and B is false (or not present), A is false (or not present) and B is true (or present), and both A and B are true (or present).

The use of "a" or "an" to describe the various elements and components herein is merely for convenience and to give a general sense of the disclosure. This description should be read to include one or at least one and the singular also includes the plural unless it is obvious that it is meant otherwise.

The term "substantial", as used herein, unless otherwise defined herein, means that greater than about 90% of the referenced material, preferably greater than about 95% of the referenced material, and more preferably greater than about 97% of the referenced material. If not specified, the percent is on a molar basis when reference is made to a molecule (such as methane, carbon dioxide, carbon monoxide and hydrogen sulfide), and otherwise is on a weight basis (such as for entrained fines).

The term "predominant portion", as used herein, unless otherwise defined herein, means that greater than 50% of the referenced material. If not specified, the percent is on a molar basis when reference is made to a molecule (such as hydrogen, methane, carbon dioxide, carbon monoxide and hydrogen sulfide), and otherwise is on a weight basis (such as for entrained fines).

The term "depleted" is synonymous with reduced from originally present. For example, removing a substantial portion of a material from a stream would produce a material-depleted stream that is substantially depleted of that material. Conversely, the term "enriched" is synonymous with greater than originally present.

The term "carbonaceous" as used herein is synonymous with hydrocarbon.

The term "carbonaceous material" as used herein is a material containing organic hydrocarbon content. Carbonaceous materials can be classified as biomass or non-biomass materials as defined herein.

The term "biomass" as used herein refers to carbonaceous materials derived from recently (for example, within the past 100 years) living organisms, including plant-based biomass and animal-based biomass. For clarification, biomass does not include fossil-based carbonaceous materials, such as coal. For example, see previously incorporated US2009/0217575A1, US2009/0229182A1 and US2009/0217587A1.

The term "plant-based biomass" as used herein means materials derived from green plants, crops, algae, and trees, such as, but not limited to, sweet sorghum, bagasse, sugarcane, bamboo, hybrid poplar, hybrid willow, albizia trees, eucalyptus, alfalfa, clover, oil palm, switchgrass, sudangrass, millet, jatropha, and miscanthus (e.g., Miscanthus×giganteus). Biomass further include wastes from agricultural cultivation, processing, and/or degradation such as corn cobs and husks, corn stover, straw, nut shells, vegetable oils, canola oil, rapeseed oil, biodiesels, tree bark, wood chips, sawdust, and yard wastes.

The term "animal-based biomass" as used herein means wastes generated from animal cultivation and/or utilization. For example, biomass includes, but is not limited to, wastes from livestock cultivation and processing such as animal manure, guano, poultry litter, animal fats, and municipal solid wastes (e.g., sewage).

The term "non-biomass", as used herein, means those carbonaceous materials which are not encompassed by the term "biomass" as defined herein. For example, non-biomass include, but is not limited to, anthracite, bituminous coal, sub-bituminous coal, lignite, petroleum coke, asphaltenes, liquid petroleum residues or mixtures thereof. For example, see US2009/0166588A1, US2009/0165379A1, US2009/0165380A1, US2009/0165361A1, US2009/0217590A1 and US2009/0217586A1.

"Liquid heavy hydrocarbon materials" are viscous liquid or semi-solid materials that are flowable at ambient conditions or can be made flowable at elevated temperature conditions. These materials are typically the residue from the processing of hydrocarbon materials such as crude oil. For example, the first step in the refining of crude oil is normally a distillation to separate the complex mixture of hydrocarbons into fractions of differing volatility. A typical first-step distillation requires heating at atmospheric pressure to vaporize as much of the hydrocarbon content as possible without exceeding an actual temperature of about 650° F., since higher temperatures may lead to thermal decomposition. The fraction which is not distilled at atmospheric pressure is commonly referred to as "atmospheric petroleum residue". The fraction may be further distilled under vacuum, such that an actual temperature of up to about 650° F. can vaporize even more material. The remaining undistillable liquid is referred to as "vacuum petroleum residue". Both atmospheric petroleum residue and vacuum petroleum residue are considered liquid heavy hydrocarbon materials for the purposes of the present invention.

Non-limiting examples of liquid heavy hydrocarbon materials include vacuum resids; atmospheric resids; heavy and reduced petroleum crude oils; pitch, asphalt and bitumen (naturally occurring as well as resulting from petroleum refining processes); tar sand oil; shale oil; bottoms from catalytic cracking processes; coal liquefaction bottoms; and other hydrocarbon feedstreams containing significant amounts of heavy or viscous materials such as petroleum wax fractions.

The term "asphaltene" as used herein is an aromatic carbonaceous solid at room temperature, and can be derived, for example, from the processing of crude oil and crude oil tar sands. Asphaltenes may also be considered liquid heavy hydrocarbon feedstocks.

The liquid heavy hydrocarbon materials may inherently contain minor amounts of solid carbonaceous materials, such as petroleum coke and/or solid asphaltenes, that are generally dispersed within the liquid heavy hydrocarbon matrix, and that remain solid at the elevated temperature conditions utilized as the feed conditions for the present process.

The terms "petroleum coke" and "petcoke" as used herein include both (i) the solid thermal decomposition product of high-boiling hydrocarbon fractions obtained in petroleum processing (heavy residues—"resid petcoke"); and (ii) the solid thermal decomposition product of processing tar sands (bituminous sands or oil sands—"tar sands petcoke"). Such carbonization products include, for example, green, calcined, needle and fluidized bed petcoke.

Resid petcoke can also be derived from a crude oil, for example, by coking processes used for upgrading heavy-gravity residual crude oil (such as a liquid petroleum residue), which petcoke contains ash as a minor component, typically about 1.0 wt % or less, and more typically about 0.5 wt % of less, based on the weight of the coke. Typically, the ash in such lower-ash cokes predominantly comprises metals such as nickel and vanadium.

Tar sands petcoke can be derived from an oil sand, for example, by coking processes used for upgrading oil sand. Tar sands petcoke contains ash as a minor component, typically in the range of about 2 wt % to about 12 wt %, and more typically in the range of about 4 wt % to about 12 wt %, based on the overall weight of the tar sands petcoke. Typically, the ash in such higher-ash cokes predominantly comprises materials such as silica and/or alumina.

Petroleum coke can comprise at least about 70 wt % carbon, at least about 80 wt % carbon, or at least about 90 wt % carbon, based on the total weight of the petroleum coke. Typically, the petroleum coke comprises less than about 20 wt % inorganic compounds, based on the weight of the petroleum coke.

The term "coal" as used herein means peat, lignite, sub-bituminous coal, bituminous coal, anthracite, or mixtures thereof. In certain embodiments, the coal has a carbon content of less than about 85%, or less than about 80%, or less than about 75%, or less than about 70%, or less than about 65%, or less than about 60%, or less than about 55%, or less than about 50% by weight, based on the total coal weight. In other embodiments, the coal has a carbon content ranging up to about 85%, or up to about 80%, or up to about 75% by weight, based on the total coal weight. Examples of useful coal include, but are not limited to, Illinois #6, Pittsburgh #8, Beulah (ND), Utah Blind Canyon, and Powder River Basin (PRB) coals. Anthracite, bituminous coal, sub-bituminous coal, and lignite coal may contain about 10 wt %, from about 5 to about 7 wt %, from about 4 to about 8 wt %, and from about 9 to about 11 wt %, ash by total weight of the coal on a dry basis, respectively. However, the ash content of any particular coal source will depend on the rank and source of the coal, as is familiar to those skilled in the art. See, for example, "Coal Data: A Reference", Energy Information Administration, Office of Coal, Nuclear, Electric and Alternate Fuels, U.S. Department of Energy, DOE/EIA-0064(93), February 1995.

The ash produced from combustion of a coal typically comprises both a fly ash and a bottom ash, as is familiar to those skilled in the art. The fly ash from a bituminous coal can comprise from about 20 to about 60 wt % silica and from about 5 to about 35 wt % alumina, based on the total weight of the fly ash. The fly ash from a sub-bituminous coal can comprise from about 40 to about 60 wt % silica and from about 20 to about 30 wt % alumina, based on the total weight of the fly ash. The fly ash from a lignite coal can comprise from about 15 to about 45 wt % silica and from about 20 to about 25 wt % alumina, based on the total weight of the fly ash. See, for example, Meyers, et al. "Fly Ash. A Highway Construction Material," Federal Highway Administration, Report No. FHWA-IP-76-16, Washington, D.C., 1976.

The bottom ash from a bituminous coal can comprise from about 40 to about 60 wt % silica and from about 20 to about 30 wt % alumina, based on the total weight of the bottom ash. The bottom ash from a sub-bituminous coal can comprise from about 40 to about 50 wt % silica and from about 15 to about 25 wt % alumina, based on the total weight of the bottom ash. The bottom ash from a lignite coal can comprise from about 30 to about 80 wt % silica and from about 10 to about 20 wt % alumina, based on the total weight of the bottom ash. See, for example, Moulton, Lyle K. "Bottom Ash and Boiler Slag," Proceedings of the Third International Ash Utilization Symposium, U.S. Bureau of Mines, Information Circular No. 8640, Washington, D.C., 1973.

A material such as methane can be biomass or non-biomass under the above definitions depending on its source of origin.

A "non-gaseous" material is substantially a liquid, semi-solid, solid or mixture at ambient conditions. For example, coal, petcoke, asphaltene and liquid petroleum residue are non-gaseous materials, while methane and natural gas are gaseous materials.

The term "unit" refers to a unit operation. When more than one "unit" is described as being present, those units are operated in a parallel fashion unless otherwise stated. A single "unit", however, may comprise more than one of the units in series, or in parallel, depending on the context. For example, an acid gas removal unit may comprise a hydrogen sulfide removal unit followed in series by a carbon dioxide removal unit. As another example, a contaminant removal unit may comprise a first removal unit for a first contaminant followed in series by a second removal unit for a second contaminant. As yet another example, a compressor may comprise a first compressor to compress a stream to a first pressure, followed in series by a second compressor to further compress the stream to a second (higher) pressure.

The term "a portion of the carbonaceous feedstock" refers to carbon content of unreacted feedstock as well as partially reacted feedstock, as well as other components that may be derived in whole or part from the carbonaceous feedstock (such as carbon monoxide, hydrogen and methane). For example, "a portion of the carbonaceous feedstock" includes carbon content that may be present in by-product char and recycled fines, which char is ultimately derived from the original carbonaceous feedstock.

The term "superheated steam" in the context of the present invention refers to a steam stream that is non-condensing under the conditions utilized, as is commonly understood by persons of ordinary skill in the relevant art.

The term "dry saturated steam" or "dry steam" in the context of the present invention refers to slightly superheated saturated steam that is non-condensing, as is commonly understood by persons of ordinary skill in the relevant art.

The term "syngas demand" refers to the maintenance of syngas balance in the hydromethanation reactor for the hydromethanation reaction of step (c). As indicated above, in the overall desirable steady-state hydromethanation reaction (see equations (I), (II) and (III) above), hydrogen and carbon monoxide are generated and consumed in relative balance. Because both hydrogen and carbon monoxide are withdrawn as part of the gaseous products, hydrogen and carbon monoxide must be added to (via a superheated syngas feed stream (16) in FIGS. 1 and 2, and as discussed below) and/or generated in situ (via a combustion/oxidation reaction with supplied oxygen as discussed below) the hydromethanation reactor in an amount at least required to substantially maintain this reaction balance. For the purposes of the present invention, the amount of hydrogen and carbon monoxide that must be added to and/or generated in situ for the hydromethanation reaction (step (c)) is the "syngas demand".

The term "steam demand" refers to the amount of steam that must be added to the hydromethanation reactor via the gas feed streams to the hydromethanation reactor. Steam is consumed in the hydromethanation reaction and some steam must be added to the hydromethanation reactor. The theoretical consumption of steam is two moles for every two moles of carbon in the feed to produce one mole of methane and one mole of carbon dioxide (see equation (V)). In actual practice, the steam consumption is not perfectly efficient and steam is withdrawn with the product gases; therefore, a greater than theoretical amount of steam needs to be added to the hydromethanation reactor, which added amount is the "steam demand". Steam can be added, for example, via the steam stream and the oxygen-rich gas stream (which are typically combined prior to introduction into the hydromethanation reactor as discussed below), as well as via the stripping gas fed to the char-withdrawal standpipes. The amount of steam to be added (and the source) is discussed in further detail below. Steam generated in situ from the carbonaceous feedstock (e.g., from vaporization of any moisture content of the carbonaceous feedstock, or from an oxidation reaction with hydrogen, methane and/or other hydrocarbons present in or generated from the carbonaceous feedstock) can assist in providing steam; however, it should be noted that any steam generated in situ or fed into the hydromethanation reactor at a temperature lower than the operating temperature within the hydromethanation reactor (the hydromethanation reaction temperature) will have an impact on the "heat demand" for the hydromethanation reaction.

The term "heat demand" refers to the amount of heat energy that must be added to the hydromethanation reactor and/or generated in situ (for example, via a combustion/oxidation reaction with supplied oxygen as discussed below) to keep the reaction of step (c) in substantial thermal balance, as discussed above and as further detailed below. In the context of the present invention, as discussed below, in steady-state operation of the process, all streams (with the potential exception of the stripped gas stream if oxygen is part of the stripping gas) are typically fed into the hydromethanation reactor at a temperature below the operating temperature of the hydromethanation reaction (step (c)). In that case the "heat demand" will be substantially satisfied by the in situ combustion/oxidation reaction with supplied oxygen (including an oxygen/combustion that occurs as a result of using oxygen as a component of the stripping gas).

Although methods and materials similar or equivalent to those described herein can be used in the practice or testing of the present disclosure, suitable methods and materials are described herein. The materials, methods, and examples herein are thus illustrative only and, except as specifically stated, are not intended to be limiting.

General Process Information

Figure 2:
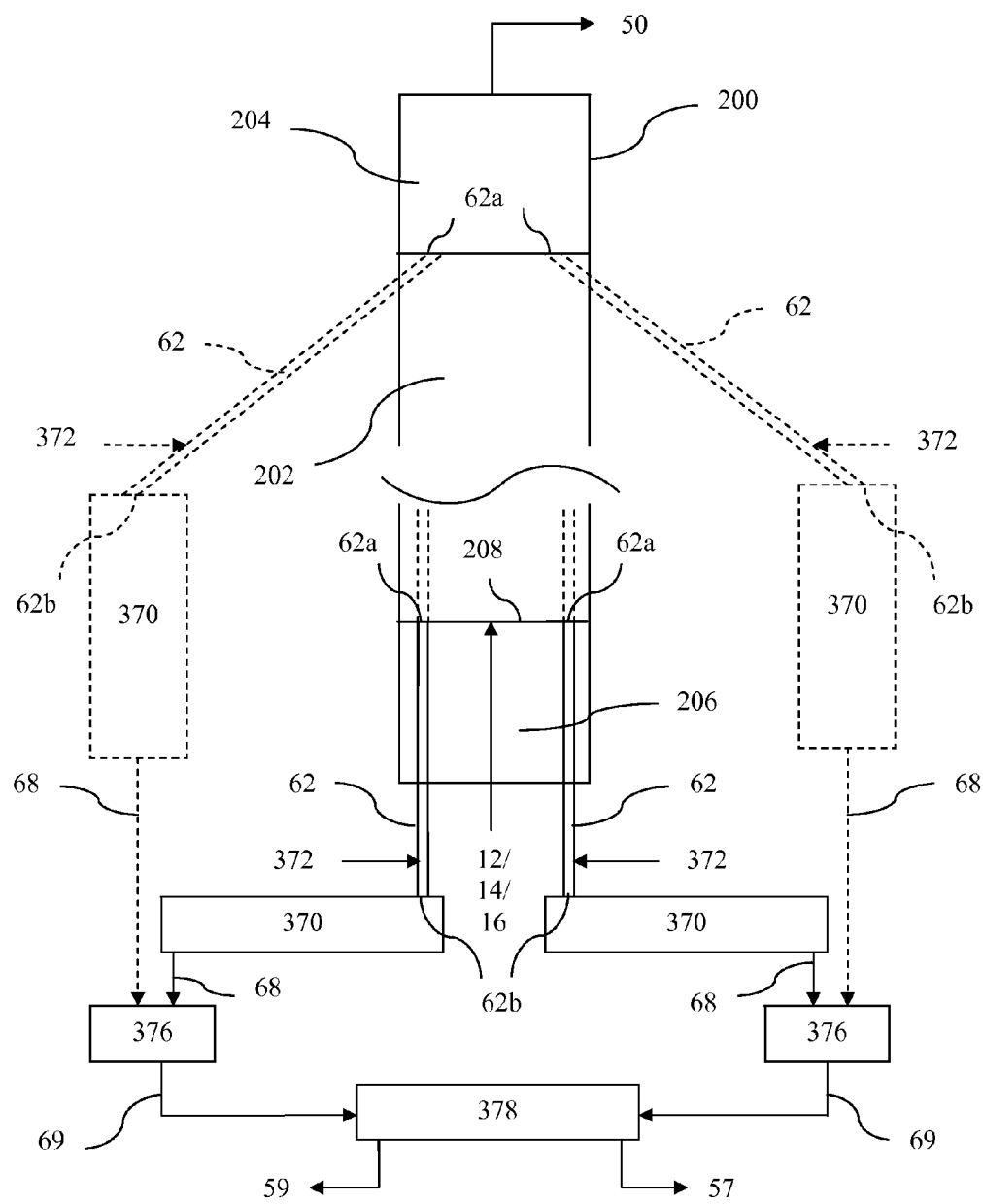
FIG. 2 is a more detailed diagram of an embodiment of the process of the present invention showing examples of different potential configurations of the char discharge unit.

In one embodiment of the invention, a methane-enriched raw product gas stream (50) and a gas-stripped char stream (68) are ultimately generated from a non-gaseous carbonaceous material (10) as illustrated in FIGS. 1 and 2.

Referring to FIG. 1, in accordance with an embodiment of the invention, the non-gaseous carbonaceous material (10) is processed in a feedstock preparation unit (100) to generate a carbonaceous feedstock (32) which is fed to a catalyst application unit (350) where hydromethanation catalyst is applied to generate a catalyzed carbonaceous feedstock (31+32).

In certain optional embodiments as discussed below, all or a portion of a recycle carbon-enriched and inorganic ash-depleted char stream (65) and/or all or a portion of a recovered fines stream (362) may be (i) fed to feedstock preparation unit (100) and co-processed with the non-gaseous carbonaceous material (10), (ii) combined with carbonaceous feedstock (32) for feeding to catalyst application unit (350), (iii) combined with catalyzed carbonaceous feedstock (31+32); or (iv) some combination of the above may be utilized.

The hydromethanation catalyst will typically comprise a recycle catalyst from recycle catalyst stream (57) and a makeup catalyst from make-up catalyst stream (56). Further details are provided below.

The catalyzed carbonaceous feedstock (31+32) is fed into a hydromethanation reactor (200) along with a steam stream (12), and one or both of an oxygen-rich gas stream (14) and a superheated syngas feed stream (16).

Steam stream (12) is desirably generated from process heat recovery (e.g., from heat energy recovery from the hot raw product gas) such that the process is steam integrated.

The steam stream (12), oxygen-rich gas stream (14) and superheated syngas feed stream (16) may be a single feed stream which comprises, or multiple feed streams which comprise, in combination with the in situ generation of heat energy and syngas, steam and heat energy, and optionally hydrogen and carbon monoxide, as required to at least substantially satisfy, or at least satisfy, the syngas, steam and heat demands of the hydromethanation reaction that takes place in hydromethanation reactor (200).

In the hydromethanation reactor (200), (i) a portion of the carbonaceous feedstock, steam, hydrogen and carbon monoxide react in the presence of the hydromethanation catalyst to generate a methane-enriched raw product gas (the hydromethanation reaction), and (ii) when oxygen is fed into the hydromethanation reactor (200), a portion of the carbonaceous feedstock reacts with oxygen to generate heat energy and typically carbon monoxide, hydrogen and carbon dioxide (combustion/oxidation reaction). The generated methane-enriched raw product gas is withdrawn as a methane-enriched raw product gas stream (50) from the hydromethanation reactor (200). The withdrawn methane-enriched raw product gas stream (50) typically comprises at least methane, carbon monoxide, carbon dioxide, hydrogen, hydrogen sulfide, steam, entrained solids fines and heat energy.

The hydromethanation reactor (200) comprises a fluidized bed (202). Desirably, oxygen is fed into a lower portion (202a) of the fluidized bed (200), resulting in fluidized bed having an upper portion (202b) and a lower portion (202a). Without being bound by any particular theory, the hydromethanation reaction predominates in upper portion (202b), and an oxidation reaction with the oxygen from oxygen-rich gas stream (14) predominates in lower portion (202a). It is believed that there is no specific defined boundary between the two portions, but rather there is a transition as oxygen is consumed (and heat energy and syngas are generated) in lower portion (202a). It is also believed that oxygen consumption is rapid under the conditions present in hydromethanation reactor (200); therefore, the predominant portion of fluidized bed (202) will be upper portion (202b).

As discussed below, a portion of the oxygen-rich gas stream (14) (and the steam stream (12)) can also be fed via a char-withdrawal standpipe (see (62) in FIG. 2), for example, as all or part of the stripping gas (step (f)).

The steam stream (12) and oxygen-rich gas stream (14) may be fed separately into the hydromethanation reactor (200), but are typically combined prior to feeding into lower portion (202a) of fluidized bed (202). In one embodiment, as disclosed in previously incorporated US2012/0046510A1, superheated syngas feed stream (16) is not present, and the catalyzed carbonaceous feedstock (31+32), steam stream (12) and oxygen-rich gas stream (14) are all fed to hydromethanation reactor (200) at a temperature below the target operating temperature of the hydromethanation reaction.

At least a portion of the carbonaceous feedstock in lower portion (202a) of fluidized bed (202) (and optionally in char-withdrawal standpipe (62)) will react with oxygen from oxygen-rich gas stream (14) to generate heat energy, and also hydrogen and carbon monoxide (syngas). In one embodiment, this occurs in sufficient amounts to satisfy the heat and syngas demands of the hydromethanation reaction (no separate superheated syngas feed stream (16) is utilized in steady-state operation of the process). This includes the reaction of solid carbon from unreacted (fresh) feedstock, partially reacted feedstock (such as char and recycled fines), as well gases (carbon monoxide, hydrogen, methane and higher hydrocarbons) that may be generated from or carried with the feedstock and recycle fines in lower portion (202a). Generally some water (steam) may be produced, as well as other by-products such as carbon dioxide depending on the extent of combustion/oxidation.

As indicated above, in hydromethanation reactor (200) (predominantly in upper portion (202b) of fluidized bed (202)) the carbonaceous feedstock, steam, hydrogen and carbon monoxide react in the presence of the hydromethanation catalyst to generate a methane-enriched raw product, which is ultimately withdrawn as a methane-enriched raw product stream (50) from the hydromethanation reactor (200).

The reactions of the carbonaceous feedstock in fluidized bed (202) also result in a by-product char comprising unreacted carbon as well as non-carbon content from the carbonaceous feedstock (including entrained hydromethanation catalyst) as described in further detail below. To prevent buildup of the residue in the hydromethanation reactor (200), a solid purge of by-product char is routinely withdrawn (periodically or continuously) via a char withdrawal line (58).

In accordance with the present invention, and as depicted in FIG. 2, the char withdrawal line (58 from FIG. 1) comprises one or more char-withdrawal standpipes (62) that have a withdrawal end (62a) and a discharge end (62b). In char-withdrawal standpipe (62), the withdrawn char flows from withdrawal end (62a) to discharge end (62b). Char-withdrawal standpipe (62) can be any pipe or other conduit through which char can be removed from hydromethanation reactor (200) and transported to screw discharge unit (370) at elevated temperature and pressure.

A stripping gas feed line (372) is fluidly connected to char-withdrawal standpipe (62), typically closer to the discharge end (62a), for flowing a stripping gas in a direction countercurrent to the flow of the withdrawn char. The stripping gas assists in removing entrained gases from the withdrawn char, and generates a stripped gas stream enriched in the entrained gases, which is returned to hydromethanation reactor (200) via char-withdrawal standpipe (62), as well as a gas-stripped char stream depleted in the entrained gases.

The stripping gas is desirably used in an amount sufficient to keep the withdrawn char in char-withdrawal standpipe in a fluid (or fluidized) state to prevent any agglomeration of the char and/or clogging the char-withdrawal standpipe (62). In the event of reduced flow or clogging of char-withdrawal standpipe (62), the stripping gas can also be fed in at higher pressures and/or pulsed to assist in removal of any blockage.

Typically, the stripping gas will comprises one or both of steam and carbon dioxide, and optionally oxygen. For example, a portion of steam stream (12) and oxygen-rich gas stream (14) can be fed via char-withdrawal standpipe (62). Alternatively, carbon dioxide recovered from a downstream acid gas removal process can be utilized as the stripping gas, optionally combined with oxygen and/or steam.

The gas-stripped char stream is fed into a screw discharge unit (370) in communication with discharge end (62b) of char withdrawal standpipe (62). As discussed in more detail below, there is typically one screw discharge unit (370) for each char-withdrawal standpipe (62), and there may be single or multiple of each combination. The withdrawal end (62a) of each char-withdrawal standpipe (62) may be placed at any point above, at and/or below the fluidized bed (202) within hydromethanation reactor (200), and each char-withdrawal standpipe (62) will typically be individually oriented vertically and/or at an angle depending on placement within hydromethanation reactor (200) and location of the corresponding screw discharge unit (370). Likewise, each screw discharge unit (370) may individually be oriented vertically, horizontally or at an angle.

In addition to the transport of the char, a screw discharge unit (370) can also assist in processing larger or agglomerated particles (often referred to as "clinkers") to reduce particle size, as well as reducing the volume of the transported char by "squeezing" out entrained gases, which are ultimately returned to hydromethanation reactor (200) as part of the stripped gas stream.

As also discussed below, in one embodiment one or all of the screw discharge units (370) is a cooling screw discharge unit.

The by-product char, including gas-stripped char (68) discharged from each screw discharge unit (370), can be processed in a catalyst recovery unit (300) to recover entrained catalyst, and optionally other value-added by-products such as vanadium and nickel (depending on the content of the non-gaseous carbonaceous material (10)), to generate a depleted char (59). Depleted char (59) may optionally processed in a carbon recovery unit (325) to generate the recycle carbon-enriched and inorganic ash-depleted char stream (65) and a carbon-depleted and inorganic ash-enriched stream (66), as disclosed in U.S. patent application Ser. No. 13/450, 995 (incorporated below). In another embodiment, all or a portion of the recovered fines stream (362) may be co-processed with the withdrawn by-product char in catalyst recovery unit (300).

In one embodiment as disclosed in previously incorporated US2012/0102836A1, carbonaceous feedstock (32) (or catalyzed carbonaceous feedstock (31+32)) is fed into lower portion (202a) of fluidized bed (202). Because catalyzed carbonaceous feedstock (31+32) is introduced into lower portion (202a) of fluidized bed (202), at least one char withdrawal line (58) (at least one withdrawal end (62a) of a char-withdrawal standpipe (62)) will be located at a point such that by-product char is withdrawn from fluidized bed (202) at one or more points above the feed location of catalyzed carbonaceous feedstock (31+32), typically from upper portion (202b) of fluidized bed (202).

In this embodiment, due to the lower feed point of catalyzed carbonaceous feedstock (31+32) into hydromethanation reactor (200), and higher withdrawal point of by-product char from hydromethanation reactor (200), hydromethanation reactor (200) with be a flow-up configuration as discussed below.

Hydromethanation reactor (200) also typically comprises a zone (206) below fluidized-bed (202), with the two sections typically being separated by a grid plate (208) or similar divider (for example, an array of sparger pipes). Particles too large to be fluidized in fluidized-bed section (202), for example large-particle by-product char and non-fluidizable agglomerates, are generally collected in lower portion (202a) of fluidized bed (202), as well as zone (206). Such particles will typically comprise a carbon content (as well as an ash and catalyst content), and may be removed periodically from hydromethanation reactor (200) via a char withdrawal line (58) for catalyst recovery and further processing. In one embodiment, there is a withdrawal end (62a) of at least one char-withdrawal standpipe (62) in lower portion (202a) fluidized bed (202), typically at or just above grid plate (208), for withdrawal of this larger-particle by-product char (and other char as well).

Typically, the methane-enriched raw product passes through an initial disengagement zone (204) above the fluidized-bed section (202) prior to withdrawal from hydromethanation reactor (200). The disengagement zone (204) may optionally contain, for example, one or more internal cyclones and/or other entrained particle disengagement mechanisms. The "withdrawn" (see discussion below) methane-enriched raw product gas stream (50) typically comprises at least methane, carbon monoxide, carbon dioxide, hydrogen, hydrogen sulfide, steam, heat energy and entrained fines.

The methane-enriched raw product gas stream (50) is initially treated to remove a substantial portion of the entrained fines, typically via a cyclone assembly (360) (for example, one or more internal and/or external cyclones), which may be followed if necessary by optional additional treatments such as Venturi scrubbers, as discussed in more detail below. The "withdrawn" methane-enriched raw product gas stream (50), therefore, is to be considered the raw product prior to fines separation, regardless of whether the fines separation takes place internal to and/or external of hydromethanation reactor (200).

As specifically depicted in FIG. 1, the methane-enriched raw product stream (50) is passed from hydromethanation reactor (200) to a cyclone assembly (360) for entrained particle separation. While cyclone assembly (360) is shown in FIG. 1 as a single external cyclone for simplicity, as indicated above cyclone assembly (360) may be an internal and/or external cyclone, and may also be a series of multiple internal and/or external cyclones.

The methane-enriched raw product gas stream (50) is treated in cyclone assembly (360) to generate a fines-depleted methane-enriched raw product gas stream (52) and a recovered fines stream (362).

Recovered fines stream (362) may be fed back into hydromethanation reactor (202), for example, into upper portion (202b) of fluidized bed (202) via fines recycle line (364), and/or into lower portion (202a) of fluidized bed (202) via fines recycle line (366) (as disclosed in previously incorporated US2012/0060417A1). To the extent not fed back into fluidized bed (202), recovered fines stream (362) may, for example, be recycled back to feedstock preparation unit (100) and/or catalyst recovery unit (300), and/or combined with catalyzed carbonaceous feedstock (31+32). A screw discharge unit (370a) may also be used in connection with the transport of recovered fines stream (362), for example, for transport to catalyst recovery unit (300).

The fines-depleted methane-enriched raw product gas stream (52) typically comprises at least methane, carbon monoxide, carbon dioxide, hydrogen, hydrogen sulfide, steam, ammonia and heat energy, as well as small amounts of contaminants such as remaining residual entrained fines, and other volatilized and/or carried material (for example, mercury) that may be present in the carbonaceous feedstock. There are typically virtually no (total typically less than about 50 ppm) condensable (at ambient conditions) hydrocarbons present in fines-depleted methane-enriched raw product gas stream (52).

The fines-depleted methane-enriched raw product gas stream (52) can be treated in one or more downstream processing steps to recover heat energy, decontaminate and convert, to one or more value-added products such as, for example, substitute natural gas (pipeline quality), hydrogen, carbon monoxide, syngas, ammonia, methanol and other syngas-derived products, electrical power and steam, as disclosed in many of the documents referenced in the "Hydromethanation" section below and as further discussed below.

Additional details and embodiments are provided below.

Hydromethanation

Catalytic gasification/hydromethanation and/or raw product conversion processes and conditions are generally disclosed, for example, in U.S. Pat. No. 3,828,474, U.S. Pat. No. 3,998,607, U.S. Pat. No. 4,057,512, U.S. Pat. No. 4,092,125, U.S. Pat. No. 4,094,650, U.S. Pat. No. 4,204,843, U.S. Pat. No. 4,468,231, U.S. Pat. No. 4,500,323, U.S. Pat. No. 4,541,841, U.S. Pat. No. 4,551,155, U.S. Pat. No. 4,558,027, U.S. Pat. No. 4,606,105, U.S. Pat. No. 4,617,027, U.S. Pat. No. 4,609,456, U.S. Pat. No. 5,017,282, U.S. Pat. No. 5,055,181, U.S. Pat. No. 6,187,465, U.S. Pat. No. 6,790,430, U.S. Pat. No. 6,894,183, U.S. Pat. No. 6,955,695, US2003/0167961A1 and US2006/0265953A1, as well as in previously incorporated US2007/0000177A1, US2007/0083072A1, US2007/0277437A1, US2009/0048476A1, US2009/0090056A1, US2009/0090055A1, US2009/0165383A1, US2009/0166588A1, US2009/0165379A1, US2009/0170968A1, US2009/0165380A1, US2009/0165381A1, US2009/0165361A1, US2009/0165382A1, US2009/0169449A1, US2009/0169448A1, US2009/0165376A1, US2009/0165384A1, US2009/0217582A1, US2009/0220406A1, US2009/0217590A1, US2009/0217586A1, US2009/0217588A1, US2009/0218424A1, US2009/0217589A1, US2009/0217575A1, US2009/0229182A1, US2009/0217587A1, US2009/0246120A1, US2009/0259080A1, US2009/0260287A1, US2009/0324458A1, US2009/0324459A1, US2009/0324460A1, US2009/0324461A1, US2009/0324462A1, US2010/0076235A1, US2010/

0071262A1, US2010/0121125A1, US2010/0120926A1, US2010/0179232A1, US2010/0168495A1, US2010/0168494A1, US2010/0292350A1, US2010/0287836A1, US2010/0287835A1, US2011/0031439A1, US2011/0062012A1, US2011/0062722A1, US2011/0062721A1, US2011/0064648A1, US2011/0088896A1, US2011/0088897A1, US2011/0146978A1, US2011/0146979A1, US2011/0207002A1, US2011/0217602A1, US2011/0262323A1, US2012/0046510A1, US2012/0060417A1, US2012/0102836A1, US2012/0102837A1 and US2012/0213680A1. See also commonly-owned U.S. patent application Ser. No. 13/450,995 (entitled HYDROMETHANATION OF A CARBONACEOUS FEEDSTOCK, which was filed 19 Apr. 2012) and Ser. No. 13/484,918 (entitled HYDROMETHANATION OF A CARBONACEOUS FEEDSTOCK, which was filed 31 May 2012).

In an embodiment in accordance with the present invention as illustrated in FIG. 1, catalyzed carbonaceous feedstock (31+32), steam stream (12) and, optionally, superheated syngas feed stream (16) are introduced into hydromethanation reactor (200). In addition, an amount of an oxygen-rich gas stream (14) is typically also introduced into hydromethanation reactor (200) for in situ generation of heat energy and syngas, as generally discussed above and disclosed in many of the previously incorporated references (see, for example, previously incorporated US2010/0076235A1, US2010/0287835A1, US2011/0062721A1, US2012/0046510A1 and US2012/0060417A1, and U.S. patent application Ser. Nos. 13/450,995 and 13/484,918).

Steam stream (12), oxygen-rich gas stream (14) and superheated syngas feed stream (16) (if present) are desirably introduced into hydromethanation reactor at a temperature below the target operating temperature of the hydromethanation reaction, as disclosed in previously incorporated US2012/0046510A1. Although under those conditions this has a negative impact on the heat demand of the hydromethanation reaction, this advantageously allows full steam/heat integration of the hydromethanation portion of the process, without the use of fuel-fired superheaters (in steady-state operation of the process) that are typically fueled with a portion of the product from the process.

Typically, superheated syngas feed stream (16) will not be present in steady-state operation of the process.

Hydromethanation reactor (200) is a fluidized-bed reactor. Hydromethanation reactor (200) can, for example, be a "flow down" countercurrent configuration, where the catalyzed carbonaceous feedstock (31+32) is introduced at a higher point so that the particles flow down the fluidized bed (202) toward lower portion (202a) of fluidized bed (202), and the gases flow in an upward direction and are removed at a point above the fluidized bed (202).

Alternatively, hydromethanation reactor (200) can have a "flow up" co-current configuration, where the catalyzed carbonaceous feedstock (31+32) is fed at a lower point (bottom portion (202a) of fluidized bed (202)) so that the particles flow up the fluidized bed (202), along with the gases, to a char by-product removal zone, for example, near or at the top of upper portion (202b) of fluidized bed (202), to the top of fluidized bed (202). In one embodiment, the feed point of the carbonaceous feedstock (such as catalyzed carbonaceous feedstock (31+32)) should result in introduction into fluidized bed (200) as close to the point of introduction of oxygen (from oxygen-rich gas stream (14)) as reasonably possible. See, for example, previously incorporated US2012/0102836A1.

Char by-product removal from hydromethanation reactor (200) can be at any desired place or places, for example, at the top of fluidized bed (202), at any place within upper portion (202b) and/or lower portion (202a) of fluidized bed (202), and/or at or just below grid plate (208). The withdrawal end (62a) of char-withdrawal standpipe (62) will be located at one or more of these desired locations. As indicated above, the location where catalyzed carbonaceous feedstock (31+32) is introduced will have an influence on the location of a char withdrawal point.

Typically, there will be at least one char withdrawal point at or below grid plate (208) to withdraw char comprising larger or agglomerated particles, as discussed above. Two examples of grid plate char withdrawal configurations are shown in FIGS. 3 and 4.

Figure 3:
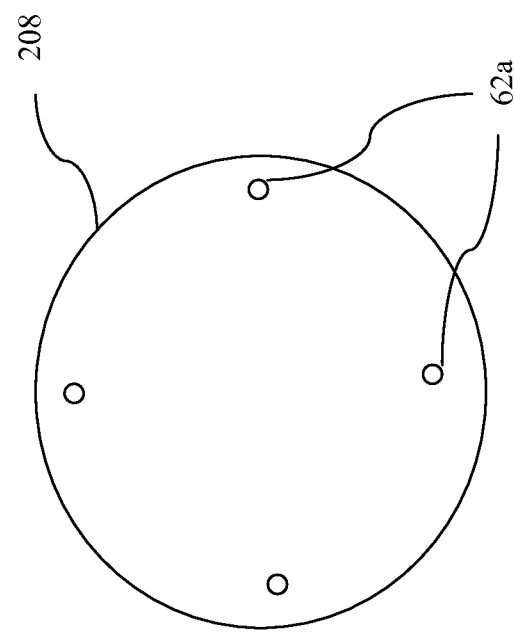
FIG. 3 is a diagram of an embodiment of the process of the present invention showing a first potential orientation of a plurality of char-withdrawal standpipes on a convex grid plate.

In FIG. 3, grid plate (208) has a convex shape, meaning that char will flow in a direction away from the center of grid plate (208). In such configuration, withdrawal end (62a) of char-withdrawal standpipe (62) will be located close to the outer edge of grid plate (208). As shown in the example of FIG. 3, there are four equally spaced withdrawal ends (62a).

Figure 4:
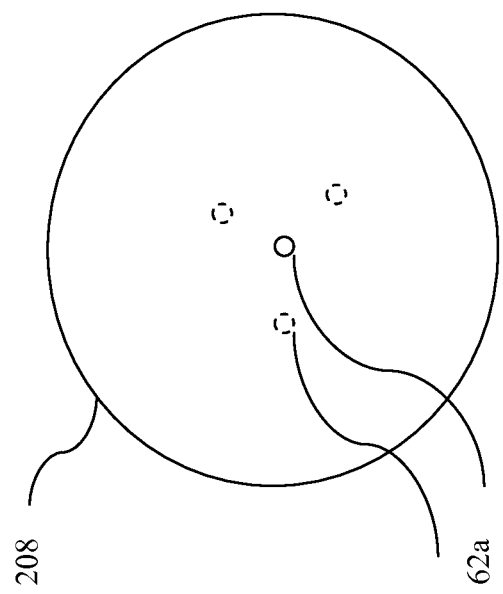
FIG. 4 is a diagram of an embodiment of the process of the present invention showing a second potential orientation of one or more char-withdrawal standpipes on a concave grid plate.

In FIG. 4, grid plate (208) has a concave shape, meaning that char will flow in a direction toward the center of grid plate (208). As such, there is a withdrawal end (62a) of a char-withdrawal standpipe (62) at the center of grid plate (208). In addition, as shown in the example of FIG. 4, there can be one or more other withdrawal ends (62a) equally spaced outside of the center of grid plate (208) for additional char withdrawal.

Hydromethanation reactor (200) is typically operated at moderately high pressures and temperatures, requiring introduction of solid streams (e.g., catalyzed carbonaceous feedstock (31+32) and if present recycle fines) to the reaction chamber of the reactor while maintaining the required temperature, pressure and flow rate of the streams. Those skilled in the art are familiar with feed inlets to supply solids into the reaction chambers having high pressure and/or temperature environments, including star feeders, screw feeders, rotary pistons and lock-hoppers. It should be understood that the feed inlets can include two or more pressure-balanced elements, such as lock hoppers, which would be used alternately. In some instances, the carbonaceous feedstock can be prepared at pressure conditions above the operating pressure of the reactor and, hence, the particulate composition can be directly passed into the reactor without further pressurization. Gas for pressurization can be an inert gas such as nitrogen, or more typically a stream of carbon dioxide that can, for example be recycled from a carbon dioxide stream generated by an acid gas removal unit.

Hydromethanation reactor (200) is desirably operated at a moderate temperature (as compared to "conventional" oxidation-based gasification processes), with an operating temperature of at least about 1000° F. (about 538° C.), or at least about 1100° F. (about 593° C.), to about 1500° F. (about 816° C.), or to about 1400° F. (about 760° C.), or to about 1300° F. (704° C.); and a pressure of about 250 psig (about 1825 kPa, absolute), or about 400 psig (about 2860 kPa), or about 450 psig (about 3204 kPa), to about 1000 psig (about 6996 kPa), or to about 800 psig (about 5617 kPa), or to about 700 psig (about 4928 kPa), or to about 600 psig (about 4238 kPa), or to about 500 psig (about 3549 kPa). In one embodiment, hydromethanation reactor (200) is operated at a pressure (first operating pressure) of up to about 600 psig (about 4238 kPa), or up to about 550 psig (about 3894 kPa).

Typical gas flow velocities in hydromethanation reactor (200) are from about 0.5 ft/sec (about 0.15 m/sec), or from about 1 ft/sec (about 0.3 m/sec), to about 2.0 ft/sec (about 0.6 m/sec), or to about 1.5 ft/sec (about 0.45 m/sec).

As oxygen-rich gas stream (14) is fed into hydromethanation reactor (200), a portion of the carbonaceous feedstock (desirably carbon from the partially reacted feedstock, by-product char and recycled fines) will be consumed in an oxidation/combustion reaction, generating heat energy as well as typically some amounts carbon monoxide and hydrogen (and typically other gases such as carbon dioxide and steam). The variation of the amount of oxygen supplied to hydromethanation reactor (200) provides an advantageous process control to ultimately maintain the syngas and heat balance. Increasing the amount of oxygen will increase the oxidation/combustion, and therefore increase in situ heat generation. Decreasing the amount of oxygen will conversely decrease the in situ heat generation. The amount of syngas generated will ultimately depend on the amount of oxygen utilized, and higher amounts of oxygen may result in a more complete combustion/oxidation to carbon dioxide and water, as opposed to a more partial combustion to carbon monoxide and hydrogen.

The amount of oxygen supplied to hydromethanation reactor (200) must be sufficient to combust/oxidize enough of the carbonaceous feedstock to generate enough heat energy and syngas to meet the heat and syngas demands of the steady-state hydromethanation reaction.

In one embodiment, a portion of oxygen-rich gas stream (14) is utilized as a component of the stripping gas, typically fed into a char withdrawal standpipe (62) via stripping gas feed line (372).

In one embodiment, the amount of molecular oxygen (as contained in the oxygen-rich gas stream (14)) that is provided to the hydromethanation reactor (200) can range from about 0.10, or from about 0.20, or from about 0.25, to about 0.6, or to about 0.5, or to about 0.4, or to about 0.35 pounds of $O_2$ per pound of carbonaceous feedstock (32).

The hydromethanation and oxidation/combustion reactions within hydromethanation reactor (200) will occur contemporaneously. Depending on the configuration of hydromethanation reactor (200), the two steps will typically predominant in separate zones—the hydromethanation in upper portion (202b) of fluidized bed (202), and the oxidation/combustion in lower portion (202a) of fluidized bed (202). The oxygen-rich gas stream (14) is typically mixed with steam stream (12) and the mixture introduced at or near the bottom of fluidized bed (202) in lower portion (202a) to avoid formation of hot spots in the reactor, and to avoid (minimize) combustion of the desired gaseous products. Feeding the catalyzed carbonaceous feedstock (31+32) with an elevated moisture content, and particularly into lower portion (202a) of fluidized bed (202), also assists in heat dissipation and the avoidance if formation of hot spots in reactor (200), as disclosed in previously incorporated US2012/0102837A1.

If superheated syngas feed stream (16) is present, that stream will typically be introduced as a mixture with steam stream (12), with oxygen-rich gas stream (14) introduced separately into lower portion (202a) of fluidized bed (202) so as to not preferentially consume the syngas components.

The oxygen-rich gas stream (14) can be fed into hydromethanation reactor (200) by any suitable means such as direct injection of purified oxygen, oxygen-air mixtures, oxygen-steam mixtures, or oxygen-inert gas mixtures into the reactor. See, for instance, US4315753 and Chiaramonte et al., Hydro carbon Processing, September 1982, pp. 255-257.

The oxygen-rich gas stream (14) is typically generated via standard air-separation technologies, and will be fed mixed with steam, and introduced at a temperature above about 250° F. (about 121° C.), to about 400° F. (about 204° C.), or to about 350° F. (about 177° C.), or to about 300° F. (about 149° C.), and at a pressure at least slightly higher than present in hydromethanation reactor (200). The steam in oxygen-rich gas stream (14) should be non-condensable during transport of oxygen-rich stream (14) to hydromethanation reactor (200), so oxygen-rich stream (14) may need to be transported at a lower pressure then pressurized (compressed) just prior to introduction into hydromethanation reactor (200).

As indicated above, the hydromethanation reaction has a steam demand, a heat demand and a syngas demand. These conditions in combination are important factors in determining the operating conditions for the hydromethanation reaction as well as the remainder of the process.

For example, the hydromethanation reaction requires a theoretical molar ratio of steam to carbon (in the feedstock) of at least about 1. Typically, however, the molar ratio is greater than about 1, or from about 1.5 (or greater), to about 6 (or less), or to about 5 (or less), or to about 4 (or less), or to about 3 (or less), or to about 2 (or less). The moisture content of the catalyzed carbonaceous feedstock (31+32), moisture generated from the carbonaceous feedstock in the hydromethanation reactor (200), and steam included in the steam stream (12), oxygen-rich gas stream (14) and recycle fines stream(s) (and optional superheated syngas feed stream (16)), all contribute steam for the hydromethanation reaction. The steam in steam stream (12) should be sufficient to at least substantially satisfy (or at least satisfy) the "steam demand" of the hydromethanation reaction.

As also indicated above, the hydromethanation reaction is essentially thermally balanced but, due to process heat losses and other energy requirements (for example, vaporization of moisture on the feedstock), some heat must be generated in the hydromethanation reaction to maintain the thermal balance (the heat demand). The partial combustion/oxidation of carbon in the presence of the oxygen introduced into hydromethanation reactor (200) from oxygen-rich gas stream (14) should be sufficient to at least substantially satisfy (or at least satisfy) both the heat and syngas demand of the hydromethanation reaction.

The gas utilized in hydromethanation reactor (200) for pressurization and reaction of the catalyzed carbonaceous feedstock (31+32) comprises the steam stream (12) and oxygen-rich gas stream (14) (and optional superheated syngas feed stream (16)) and, optionally, additional nitrogen, air, or inert gases such as argon, which can be supplied to hydromethanation reactor (200) according to methods known to those skilled in the art. As a consequence, steam stream (12) and oxygen-rich gas stream (14) must be provided at a higher pressure which allows them to enter hydromethanation reactor (200).

In one embodiment, all streams should be fed into hydromethanation reactor (200) at a temperature less than the target operating temperature of the hydromethanation reactor, such as disclosed in previously incorporated US2012/0046510A1 (with the possible exception of the stripping gas stream when oxygen is a component of the stripping gas).

Steam stream (12) will be at a temperature above the saturation point at the feed pressure. When fed into hydromethanation reactor (200), steam stream (12) should be a superheated steam stream to avoid the possibility of any condensation occurring. Typical feed temperatures of steam stream (12) are from about 400° F. (about 204° C.), or from about 450° F. (about 232° C.), to about 650° F. (about 343° C.), or to about 600° F. (about 316° C.). Typical feed pressures of steam stream (12) are about 25 psi (about 172 kPa) or greater than the pressure within hydromethanation reactor (200).

The actual temperature and pressure of steam stream (12) will ultimately depend on the level of heat recovery from the process and the operating pressure within hydromethanation reactor (200), as discussed below. In any event, desirably no fuel-fired superheater should be used in the superheating of steam stream (12) in steady-state operation of the process.

When steam stream (12) and oxygen-rich stream (14) are combined for feeding into lower section (202a) of fluidized bed (202), the temperature of the combined stream will be controlled by the temperature of steam stream (12), and will typically range from about from about from about 400° F. (about 204° C.), or from about 450° F. (about 232° C.), to about 650° F. (about 343° C.), or to about 600° F. (about 316° C.).

The temperature in hydromethanation reactor (200) can be controlled, for example, by controlling the amount and temperature of steam stream (12), as well as the amount of oxygen supplied to hydromethanation reactor (200).

In steady-state operation, steam for the hydromethanation reaction is desirably solely generated from other process operations through process heat capture (such as generated in a waste heat boiler, generally referred to as "process steam" or "process-generated steam"), specifically from the cooling of the raw product gas in a heat exchanger unit. Additional steam can be generated for other portions of the overall process, such as disclosed, for example, in previously incorporated US2010/0287835A1 and US2012/0046510A1.

The overall process described herein is desirably steam positive, such that steam demand (pressure and amount) for the hydromethanation reaction can be satisfied via heat exchange, with process heat recovery at the different stages allowing for production of excess steam that can be used for power generation and other purposes. Desirably, process-generated steam from accounts for 100 wt % or greater of the steam demand of the hydromethanation reaction.

The result of the hydromethanation reaction is a methane-enriched raw product, which is withdrawn from hydromethanation reactor (200) as methane-enriched raw product stream (50) typically comprising $CH_4$, $CO_2$, $H_2$, CO, $H_2S$, unreacted steam and, optionally, other contaminants such as entrained fines, $NH_3$, COS, HCN and/or elemental mercury vapor, depending on the nature of the carbonaceous material utilized for hydromethanation.

If the hydromethanation reaction is run in syngas balance, the methane-enriched raw product stream (50), upon exiting the hydromethanation reactor (200), will typically comprise at least about 15 mol %, or at least about 18 mol %, or at least about 20 mol %, methane based on the moles of methane, carbon dioxide, carbon monoxide and hydrogen in the methane-enriched raw product stream (50). In addition, the methane-enriched raw product stream (50) will typically comprise at least about 50 mol % methane plus carbon dioxide, based on the moles of methane, carbon dioxide, carbon monoxide and hydrogen in the methane-enriched raw product stream (50).

If the hydromethanation reaction is run in syngas excess, e.g., contains an excess of carbon monoxide and/or hydrogen above and beyond the syngas demand (for example, excess carbon monoxide and/or hydrogen are generated due to the amount of oxygen-rich gas stream (14) fed to hydromethanation reactor (200)), then there may be some dilution effect on the molar percent of methane and carbon dioxide in methane-enriched raw product stream (50).

The non-gaseous carbonaceous materials (10) useful in these processes include, for example, a wide variety of biomass and non-biomass materials. The carbonaceous feedstock (32) is derived from one or more non-gaseous carbonaceous materials (10), which are processed in a feedstock preparation section (100) as discussed below.

The hydromethanation catalyst (31) can comprise one or more catalyst species, as discussed below.

The carbonaceous feedstock (32) and the hydromethanation catalyst (31) are typically intimately mixed (i.e., to provide a catalyzed carbonaceous feedstock (31+32)) before provision to the hydromethanation reactor (200), but they can be fed separately as well.

The hot gas effluent leaving the reaction chamber of the hydromethanation reactor (200) can pass through a fines remover unit (such as cyclone assembly (360)), incorporated into and/or external of the hydromethanation reactor (200), which serves as a disengagement zone. Particles too heavy to be entrained by the gas leaving the hydromethanation reactor (200) (i.e., fines) are returned to the hydromethanation reactor (200), for example, to the reaction chamber (e.g., fluidized bed (202)).

Residual entrained fines are substantially removed by any suitable device such as internal and/or external cyclone separators optionally followed by Venturi scrubbers to generate a fines-depleted methane-enriched raw product stream (52). As discussed above, at least a portion of these fines can be returned to lower section (202a) of fluidized bed (202) via recycle line (366). A portion may also be returned to upper portion (202b) of fluidized bed (202) via recycle line (364). Any remaining recovered fines can be processed to recover alkali metal catalyst, and/or combined at some stage with carbonaceous feedstock (32), and/or directly recycled back to feedstock preparation as described in previously incorporated US2009/0217589A1.

Removal of a "substantial portion" of fines means that an amount of fines is removed from the resulting gas stream such that downstream processing is not adversely affected; thus, at least a substantial portion of fines should be removed. Some minor level of ultrafine material may remain in the resulting gas stream to the extent that downstream processing is not significantly adversely affected. Typically, at least about 90 wt %, or at least about 95 wt %, or at least about 98 wt %, of the fines of a particle size greater than about 20 μm, or greater than about 10 μm, or greater than about 5 μm, are removed.

The resulting fines-depleted methane-enriched raw product stream (52) can be further processed for heat recovery and/or purification/conversion as required to achieve a desired end product, as disclosed in the numerous previously incorporated disclosures set forth above in the "Hydromethanation" section. Reference may be had to those disclosures for further details.

Preparation of Carbonaceous Feedstocks

Carbonaceous Materials Processing (100)

Particulate carbonaceous materials, such as biomass and non-biomass, can be prepared via crushing and/or grinding, either separately or together, according to any methods known in the art, such as impact crushing and wet or dry grinding to yield one or more carbonaceous particulates. Depending on the method utilized for crushing and/or grinding of the carbonaceous material sources, the resulting carbonaceous particulates may be sized (i.e., separated according to size) to provide the carbonaceous feedstock (32) for use in catalyst loading processes (350) to form a catalyzed carbonaceous feedstock (31+32) for the hydromethanation reactor (200).

Any method known to those skilled in the art can be used to size the particulates. For example, sizing can be performed by screening or passing the particulates through a screen or number of screens. Screening equipment can include grizzlies, bar screens, and wire mesh screens. Screens can be static or incorporate mechanisms to shake or vibrate the screen. Alternatively, classification can be used to separate the carbonaceous particulates. Classification equipment can include ore sorters, gas cyclones, hydrocyclones, rake classifiers, rotating trommels or fluidized classifiers. The carbonaceous materials can be also sized or classified prior to grinding and/or crushing.

The carbonaceous particulate can be supplied as a fine particulate having an average particle size of from about 25 microns, or from about 45 microns, up to about 2500 microns, or up to about 500 microns. One skilled in the art can readily determine the appropriate particle size for the carbonaceous particulates. For example, when a fluidized bed reactor is used, such carbonaceous particulates can have an average particle size which enables incipient fluidization of the carbonaceous materials at the gas velocity used in the fluidized bed reactor. Desirable particle size ranges for the hydromethanation reactor (200) are in the Geldart A and Geldart B ranges (including overlap between the two), depending on fluidization conditions, typically with limited amounts of fine (below about 25 microns) and coarse (greater than about 250 microns) material.

Additionally, certain carbonaceous materials, for example, corn stover and switchgrass, and industrial wastes, such as saw dust, either may not be amenable to crushing or grinding operations, or may not be suitable for use as such, for example due to ultra fine particle sizes. Such materials may be formed into pellets or briquettes of a suitable size for crushing or for direct use in, for example, a fluidized bed reactor. Generally, pellets can be prepared by compaction of one or more carbonaceous material; see for example, previously incorporated US2009/0218424A1. In other examples, a biomass material and a coal can be formed into briquettes as described in U.S. Pat. No. 4,249,471, U.S. Pat. No. 4,152,119 and U.S. Pat. No. 4,225,457. Such pellets or briquettes can be used interchangeably with the preceding carbonaceous particulates in the following discussions.

Additional feedstock processing steps may be necessary depending on the qualities of carbonaceous material sources. Biomass may contain high moisture contents, such as green plants and grasses, and may require drying prior to crushing. Municipal wastes and sewages also may contain high moisture contents which may be reduced, for example, by use of a press or roll mill (e.g., U.S. Pat. No. 4,436,028). Likewise, non-biomass, such as high-moisture coal, can require drying prior to crushing. Some caking coals can require partial oxidation to simplify operation. Non-biomass feedstocks deficient in ion-exchange sites, such as anthracites or petroleum cokes, can be pre-treated to create additional ion-exchange sites to facilitate catalyst loading and/or association. Such pre-treatments can be accomplished by any method known to the art that creates ion-exchange capable sites and/or enhances the porosity of the feedstock (see, for example, previously incorporated U.S. Pat. No. 4,468,231 and GB1599932). Oxidative pre-treatment can be accomplished using any oxidant known to the art.

The ratio and types of the carbonaceous materials in the carbonaceous particulates can be selected based on technical considerations, processing economics, availability, and proximity of the non-biomass and biomass sources. The availability and proximity of the sources for the carbonaceous materials can affect the price of the feeds, and thus the overall production costs of the catalytic gasification process. For example, the biomass and the non-biomass materials can be blended in at about 5:95, about 10:90, about 15:85, about 20:80, about 25:75, about 30:70, about 35:65, about 40:60, about 45:55, about 50:50, about 55:45, about 60:40, about 65:35, about 70:20, about 75:25, about 80:20, about 85:15, about 90:10, or about 95:5 by weight on a wet or dry basis, depending on the processing conditions.

Significantly, the carbonaceous material sources, as well as the ratio of the individual components of the carbonaceous particulates, for example, a biomass particulate and a non-biomass particulate, can be used to control other material characteristics of the carbonaceous particulates. Non-biomass materials, such as coals, and certain biomass materials, such as rice hulls, typically include significant quantities of inorganic matter including calcium, alumina and silica which form inorganic oxides (i.e., ash) in the catalytic gasifier. At temperatures above about 500° C. to about 600° C., potassium and other alkali metals can react with the alumina and silica in ash to form insoluble alkali aluminosilicates. In this form, the alkali metal is substantially water-insoluble and inactive as a catalyst. To prevent buildup of the residue in the hydromethanation reactor (200), a solid purge of by-product char (58) comprising ash, unreacted carbonaceous material, and various other compounds (such as alkali metal compounds, both water soluble and water insoluble) is withdrawn and processed as discussed below.

In preparing the carbonaceous particulates, the ash content of the various carbonaceous materials can be selected to be, for example, about 20 wt % or less, or about 15 wt % or less, or about 10 wt % or less, or about 5 wt % or less, depending on, for example, the ratio of the various carbonaceous materials and/or the starting ash in the various carbonaceous materials. In other embodiments, the resulting the carbonaceous particulates can comprise an ash content ranging from about 5 wt %, or from about 10 wt %, to about 20 wt %, or to about 15 wt %, based on the weight of the carbonaceous particulate. In other embodiments, the ash content of the carbonaceous particulate can comprise less than about 20 wt %, or less than about 15 wt %, or less than about 10 wt %, or less than about 8 wt %, or less than about 6 wt % alumina, based on the weight of the ash. In certain embodiments, the carbonaceous particulates can comprise an ash content of less than about 20 wt %, based on the weight of processed feedstock where the ash content of the carbonaceous particulate comprises less than about 20 wt % alumina, or less than about 15 wt % alumina, based on the weight of the ash.

Such lower alumina values in the carbonaceous particulates allow for, ultimately, decreased losses of catalysts, and particularly alkali metal catalysts, in the hydromethanation portion of the process. As indicated above, alumina can react with alkali source to yield an insoluble char component comprising, for example, an alkali aluminate or aluminosilicate. Such insoluble char component can lead to decreased catalyst recovery (i.e., increased catalyst loss), and thus, require additional costs of make-up catalyst in the overall process.

Additionally, the resulting carbonaceous particulates can have a significantly higher % carbon, and thus btu/lb value and methane product per unit weight of the carbonaceous particulate. In certain embodiments, the resulting carbonaceous particulates can have a carbon content ranging from about 75 wt %, or from about 80 wt %, or from about 85 wt %, or from about 90 wt %, up to about 95 wt %, based on the combined weight of the non-biomass and biomass.

In one example, a non-biomass and/or biomass is wet ground and sized (e.g., to a particle size distribution of from about 25 to about 2500 μm) and then drained of its free water (i.e., dewatered) to a wet cake consistency. Examples of suitable methods for the wet grinding, sizing, and dewatering are known to those skilled in the art; for example, see previously incorporated US2009/0048476A1. The filter cakes of the non-biomass and/or biomass particulates formed by the wet grinding in accordance with one embodiment of the present disclosure can have a moisture content ranging from about 40% to about 60%, or from about 40% to about 55%, or below 50%. It will be appreciated by one of ordinary skill in the art that the moisture content of dewatered wet ground carbonaceous materials depends on the particular type of carbonaceous materials, the particle size distribution, and the particular dewatering equipment used. Such filter cakes can be thermally treated to produce one or more reduced moisture carbonaceous particulates.

Each of the one or more carbonaceous particulates can have a unique composition, as described above. For example, two carbonaceous particulates can be utilized, where a first carbonaceous particulate comprises one or more biomass materials and the second carbonaceous particulate comprises one or more non-biomass materials. Alternatively, a single carbonaceous particulate comprising one or more carbonaceous materials utilized.

Catalyst Loading for Hydromethanation (350)

The hydromethanation catalyst is potentially active for catalyzing at least reactions (I), (II) and (III) described above. Such catalysts are in a general sense well known to those of ordinary skill in the relevant art and may include, for example, alkali metals, alkaline earth metals and transition metals, and compounds and complexes thereof. Typically, the hydromethanation catalyst comprises at least an alkali metal, such as disclosed in many of the previously incorporated references.

For the hydromethanation reaction, the one or more carbonaceous particulates are typically further processed to associate at least one hydromethanation catalyst, typically comprising a source of at least one alkali metal, to generate a catalyzed carbonaceous feedstock (31+32). If a liquid carbonaceous material is used, the hydromethanation catalyst may for example be intimately mixed into the liquid carbonaceous material.

The carbonaceous particulate provided for catalyst loading can be either treated to form a catalyzed carbonaceous feedstock (31+32) which is passed to the hydromethanation reactor (200), or split into one or more processing streams, where at least one of the processing streams is associated with a hydromethanation catalyst to form at least one catalyst-treated feedstock stream. The remaining processing streams can be, for example, treated to associate a second component therewith. Additionally, the catalyst-treated feedstock stream can be treated a second time to associate a second component therewith. The second component can be, for example, a second hydromethanation catalyst, a co-catalyst, or other additive.

In one example, the primary hydromethanation catalyst (alkali metal compound) can be provided to the single carbonaceous particulate (e.g., a potassium and/or sodium source), followed by a separate treatment to provide one or more co-catalysts and additives (e.g., a calcium source) to the same single carbonaceous particulate to yield the catalyzed carbonaceous feedstock (31+32). For example, see previously incorporated US2009/0217590A1 and US2009/0217586A1.

The hydromethanation catalyst and second component can also be provided as a mixture in a single treatment to the single second carbonaceous particulate to yield the catalyzed carbonaceous feedstock (31+32).

When one or more carbonaceous particulates are provided for catalyst loading, then at least one of the carbonaceous particulates is associated with a hydromethanation catalyst to form at least one catalyst-treated feedstock stream. Further, any of the carbonaceous particulates can be split into one or more processing streams as detailed above for association of a second or further component therewith. The resulting streams can be blended in any combination to provide the catalyzed carbonaceous feedstock (31+32), provided at least one catalyst-treated feedstock stream is utilized to form the catalyzed feedstock stream.

In one embodiment, at least one carbonaceous particulate is associated with a hydromethanation catalyst and optionally, a second component. In another embodiment, each carbonaceous particulate is associated with a hydromethanation catalyst and optionally, a second component.

Any methods known to those skilled in the art can be used to associate one or more hydromethanation catalysts with any of the carbonaceous particulates and/or processing streams. Such methods include but are not limited to, admixing with a solid catalyst source and impregnating the catalyst onto the processed carbonaceous material. Several impregnation methods known to those skilled in the art can be employed to incorporate the hydromethanation catalysts. These methods include but are not limited to, incipient wetness impregnation, evaporative impregnation, vacuum impregnation, dip impregnation, ion exchanging, and combinations of these methods.

In one embodiment, an alkali metal hydromethanation catalyst can be impregnated into one or more of the carbonaceous particulates and/or processing streams by slurrying with a solution (e.g., aqueous) of the catalyst in a loading tank. When slurried with a solution of the catalyst and/or co-catalyst, the resulting slurry can be dewatered to provide a catalyst-treated feedstock stream, again typically, as a wet cake. The catalyst solution can be prepared from any catalyst source in the present processes, including fresh or make-up catalyst and recycled catalyst or catalyst solution. Methods for dewatering the slurry to provide a wet cake of the catalyst-treated feedstock stream include filtration (gravity or vacuum), centrifugation, and a fluid press.

In another embodiment, as disclosed in previously incorporated US2010/0168495A1, the carbonaceous particulates are combined with an aqueous catalyst solution to generate a substantially non-draining wet cake, then mixed under elevated temperature conditions and finally dried to an appropriate moisture level.

One particular method suitable for combining a coal particulate and/or a processing stream comprising coal with a hydromethanation catalyst to provide a catalyst-treated feedstock stream is via ion exchange as described in previously incorporated US2009/0048476A1 and US2010/0168494A1. Catalyst loading by ion exchange mechanism can be maximized based on adsorption isotherms specifically developed for the coal, as discussed in the incorporated reference. Such loading provides a catalyst-treated feedstock stream as a wet cake. Additional catalyst retained on the ion-exchanged particulate wet cake, including inside the pores, can be controlled so that the total catalyst target value can be obtained in a controlled manner. The total amount of catalyst loaded can be controlled by controlling the concentration of catalyst components in the solution, as well as the contact time, temperature and method, as disclosed in the aforementioned incorporated references, and as can otherwise be readily determined by those of ordinary skill in the relevant art based on the characteristics of the starting coal.

In another example, one of the carbonaceous particulates and/or processing streams can be treated with the hydromethanation catalyst and a second processing stream can be treated with a second component (see previously incorporated US2007/0000177A1).

The carbonaceous particulates, processing streams, and/or catalyst-treated feedstock streams resulting from the preceding can be blended in any combination to provide the catalyzed second carbonaceous feedstock, provided at least one catalyst-treated feedstock stream is utilized to form the catalyzed carbonaceous feedstock (31+32). Ultimately, the catalyzed carbonaceous feedstock (31+32) is passed onto the hydromethanation reactor(s) (200).

Generally, each catalyst loading unit comprises at least one loading tank to contact one or more of the carbonaceous particulates and/or processing streams with a solution comprising at least one hydromethanation catalyst, to form one or more catalyst-treated feedstock streams. Alternatively, the catalytic component may be blended as a solid particulate into one or more carbonaceous particulates and/or processing streams to form one or more catalyst-treated feedstock streams.

Typically, when the hydromethanation catalyst is solely or substantially an alkali metal, it is present in the catalyzed carbonaceous feedstock in an amount sufficient to provide a ratio of alkali metal atoms to carbon atoms in the catalyzed carbonaceous feedstock ranging from about 0.01, or from about 0.02, or from about 0.03, or from about 0.04, to about 0.10, or to about 0.08, or to about 0.07, or to about 0.06.

With some feedstocks, the alkali metal component may also be provided within the catalyzed carbonaceous feedstock to achieve an alkali metal content of from about 3 to about 10 times more than the combined ash content of the carbonaceous material in the catalyzed carbonaceous feedstock, on a mass basis.

Suitable alkali metals are lithium, sodium, potassium, rubidium, cesium, and mixtures thereof. Particularly useful are potassium sources. Suitable alkali metal compounds include alkali metal carbonates, bicarbonates, formates, oxalates, amides, hydroxides, acetates, or similar compounds. For example, the catalyst can comprise one or more of sodium carbonate, potassium carbonate, rubidium carbonate, lithium carbonate, cesium carbonate, sodium hydroxide, potassium hydroxide, rubidium hydroxide or cesium hydroxide, and particularly, potassium carbonate and/or potassium hydroxide.

Optional co-catalysts or other catalyst additives may be utilized, such as those disclosed in the previously incorporated references.

The one or more catalyst-treated feedstock streams that are combined to form the catalyzed carbonaceous feedstock typically comprise greater than about 50%, greater than about 70%, or greater than about 85%, or greater than about 90% of the total amount of the loaded catalyst associated with the catalyzed carbonaceous feedstock (31+32). The percentage of total loaded catalyst that is associated with the various catalyst-treated feedstock streams can be determined according to methods known to those skilled in the art.

Separate carbonaceous particulates, catalyst-treated feedstock streams, and processing streams can be blended appropriately to control, for example, the total catalyst loading or other qualities of the catalyzed carbonaceous feedstock (31+32), as discussed previously. The appropriate ratios of the various stream that are combined will depend on the qualities of the carbonaceous materials comprising each as well as the desired properties of the catalyzed carbonaceous feedstock (31+32). For example, a biomass particulate stream and a catalyzed non-biomass particulate stream can be combined in such a ratio to yield a catalyzed carbonaceous feedstock (31+32) having a predetermined ash content, as discussed previously.

Any of the preceding catalyst-treated feedstock streams, processing streams, and processed feedstock streams, as one or more dry particulates and/or one or more wet cakes, can be combined by any methods known to those skilled in the art including, but not limited to, kneading, and vertical or horizontal mixers, for example, single or twin screw, ribbon, or drum mixers. The resulting catalyzed carbonaceous feedstock (31+32) can be stored for future use or transferred to one or more feed operations for introduction into the hydromethanation reactor(s). The catalyzed carbonaceous feedstock can be conveyed to storage or feed operations according to any methods known to those skilled in the art, for example, a screw conveyer or pneumatic transport.

In one embodiment, the carbonaceous feedstock as fed to the hydromethanation reactor contains an elevated moisture content of from greater than 10 wt %, or about 12 wt % or greater, or about 15 wt % or greater, to about 25 wt % or less, or to about 20 wt % or less (based on the total weight of the carbonaceous feedstock), to the extent that the carbonaceous feedstock is substantially free-flowing (see previously incorporated US2012/0102837A1).

The term "substantially free-flowing" as used herein means the carbonaceous feedstock particulates do not agglomerate under feed conditions due to moisture content. Desirably, the moisture content of the carbonaceous feedstock particulates is substantially internally contained so that there is minimal (or no) surface moisture.

A suitable substantially free-flowing catalyzed carbonaceous feedstock (31+32) can be produced in accordance with the disclosures of previously incorporated US2010/0168494A1 and US2010/0168495A1, where the thermal treatment step (after catalyst application) referred to in those disclosures can be minimized (or even potentially eliminated).

To the extent necessary, excess moisture can be removed from the catalyzed carbonaceous feedstock (31+32). For example, the catalyzed carbonaceous feedstock (31+32) may be dried with a fluid bed slurry drier (i.e., treatment with superheated steam to vaporize the liquid), or the solution thermally evaporated or removed under a vacuum, or under a flow of an inert gas, to provide a catalyzed carbonaceous feedstock having a the required residual moisture content.

Catalyst Recovery (300)

Reaction of the catalyzed carbonaceous feedstock (31+32) under the described conditions generally provides the methane-enriched raw product stream (50) and a solid char by-product (58).

The solid char by-product (58) typically comprises quantities of unreacted carbon, inorganic ash and entrained catalyst. The solid char by-product (58) can removed from the hydromethanation reactor (200) for sampling, purging, and/or catalyst recovery via one or more char-withdrawal standpipes (62) attached to one or more screw discharge units (370), as discussed above.

The term "entrained catalyst" as used herein means chemical compounds comprising the catalytically active portion of the hydromethanation catalyst, e.g., alkali metal compounds present in the char by-product. For example, "entrained catalyst" can include, but is not limited to, soluble alkali metal compounds (such as alkali metal carbonates, alkali metal hydroxides and alkali metal oxides) and/or insoluble alkali compounds (such as alkali metal aluminosilicates). The nature of catalyst components associated with the char extracted are discussed, for example, in previously incorporated US2007/0277437A1, US2009/0165383A1, US2009/0165382A1, US2009/0169449A1 and US2009/0169448A1.

The char by-product (58) from the hydromethanation reactor (200), including gas-stripped char (68), may be passed to a catalytic recovery unit (300), as described below. Such char by-product (58) may also be split into multiple streams, one of which may be passed to a catalyst recovery unit (300), and another stream which may be used, for example, as a methanation catalyst (as described in previously incorporated US2010/0121125A1) and not treated for catalyst recovery.

In certain embodiments, when the hydromethanation catalyst is an alkali metal, the alkali metal in the solid char by-product (58) can be recovered to produce a catalyst recycle stream (57), and any unrecovered catalyst can be compensated by a catalyst make-up stream (57) (see, for example, previously incorporated US2009/0165384A1). The more alumina plus silica that is in the feedstock, the more costly it is to obtain a higher alkali metal recovery.

In one embodiment, the solid char by-product (58) from the hydromethanation reactor (200) (gas-stripped char (68) as shown in FIG. 2) is fed to a quench tank (376) where it is quenched with an aqueous medium to extract a portion of the entrained catalyst such as, for example, as disclosed in previously incorporated US2007/0277437A1. As set forth in FIG. 2, a slurry (69) of the quenched char can then be passed to a leaching tank (378) where a substantial portion of water-insoluble entrained catalyst is converted into a soluble form, then subject to a solids/liquid separation to generate a recycle catalyst stream (57) and a depleted char stream (59) such as, for example, disclosed in previously incorporated US2009/0169449A1 and US2009/0169448A1, as well as previously incorporated US2011/0262323A1 and US2012/0213680A1.

Ultimately, the recovered catalyst (57) can be directed to the catalyst loading unit (350) for reuse of the alkali metal catalyst.

Other particularly useful recovery and recycling processes are described in U.S. Pat. No. 4,459,138, as well as previously incorporated US2007/0277437A1 US2009/0165383A1, US2009/0165382A1, US2009/0169449A1 and US2009/0169448A1. Reference can be had to those documents for further process details.

The recycle of catalyst can be to one or a combination of catalyst loading processes. For example, all of the recycled catalyst can be supplied to one catalyst loading process, while another process utilizes only makeup catalyst. The levels of recycled versus makeup catalyst can also be controlled on an individual basis among catalyst loading processes.

The by-product char (58) can also be treated for recovery of other by-products, such as vanadium and/or nickel, in addition to catalyst recovery, as disclosed in previously incorporated US2011/0262323A1 and US2012/0213680A1.

As indicated above, all or a portion of recovered fines stream (362) can be co-treated in catalyst recovery unit (300) along with by-product char (58).

The result of treatment for catalyst and other by-product recovery is a "cleaned" depleted char (59), at least a portion of which can be provided to a carbon recovery unit (325) as discussed below.

Carbon Recovery Unit (325)

In one embodiment, at least a portion, or at least a predominant portion, or at least a substantial portion, or substantially all, of the depleted char (59) can be treated in a carbon recovery unit (325) to generate a carbon-enriched and inorganic ash-depleted stream (65) and a carbon-depleted and inorganic ash-enriched stream (66), as disclosed in previously incorporated U.S. patent application Ser. No. 13/450, 995. At least a portion, or at least a predominant portion, or at least a substantial portion, or substantially all, of the carbon-enriched and inorganic ash-depleted stream (65) can be recycled back to feedstock preparation unit (100) for processing and ultimately feeding back to hydromethanation reactor (200) as part of carbonaceous feedstock (32).

Because of the carbon content of depleted char (59), it can be treated by known coal beneficiation techniques to separate a higher carbon (lower ash) fraction from a lower carbon (higher ash) fraction. The particle size of the depleted char (59) will typically be similar to or smaller than the carbonaceous feedstock (32) as provided to hydromethanation reactor (200) (below 6 mm), and thus most suited for wet beneficiation and/or magnetic separation techniques. Such techniques and equipment suitable for use in connection therewith are generally known those of ordinary skill in the relevant art, and are readily available from many commercial sources. For example, techniques and equipment such as dense-medium cyclones, hydrocyclones, wet concentration tables, cone concentrators, spiral concentrators, centrifuges and froth flotation may be utilized.

The resulting carbon-depleted and inorganic ash-enriched stream (66) will still retain some residual carbon content and can, for example, be combusted to power one or more steam generators (such as disclosed in previously incorporated US2009/0165376A1)), or used as such in a variety of applications, for example, as an absorbent (such as disclosed in previously incorporated US2009/0217582A1), or disposed of in an environmentally acceptable manner.

Screw Discharge Unit (370)

As discussed above, in accordance with the present invention at least one screw discharge unit (370) is present for transporting by-product char removed from hydromethanation reactor (200) from a discharge end (62b) of a char withdrawal standpipe (62) typically to a catalyst recovery unit (300).

Screw discharge unit (370) comprises a rotating screw in a housing that transports the char in a direction along the rotational axis of the rotating screw. The flow rate of the by-product char through screw discharge unit (370) is typically controlled by the speed of rotation of the rotating screw.

Screw discharge unit (370) is operated under pressure and at elevated temperature due to the elevated pressures and temperatures within the hydromethanation reactor. Valves may be placed before and/or after screw discharge unit (370) to assists in control of desired operating pressure of and discharge pressure from screw discharge unit (370). In one embodiment, the gas-stripped char stream (or cooled char stream if present) is discharged from the screw discharge unit at a superatmospheric pressure of at least of at least about 75%, or at least about 90%, of the operating pressure of hydromethanation reactor (200).

In one embodiment, the screw discharge unit is a cooling screw discharge unit, in which the gas-stripped char stream is cooled in the cooling screw discharge unit to generate a cooled char stream, which can be further processed as detailed above. Typically, the cooled char stream is discharged from the cooled screw discharge unit at a temperature of about 700° F. (about 371° C.) or less, or about 600° F. (about 316° C.) or less. The discharge temperature should, however, remain elevated sufficiently so that it is above the condensation temperature of water at the operating pressure of screw discharge unit (370).

The cooling screw discharge unit cools the gas-stripped char stream typically using water or steam as a heat exchange medium, although other media such as a thermal oil can also be used. In one embodiment, the cooling screw unit comprises a hollow screw member and a housing surrounding the hollow screw member, wherein the heat exchange medium is circulated through the hollow screw member, around the housing or both.

Screw discharge units and cooling screw discharge units are in a general sense known to those of ordinary skill n the relevant art, and several variations potentially adaptable for use in connection with the present invention are generally commercially available, for example, from sources such as Therma-Flite Inc. (Benecia, Calif. USA), Metso Minerals, Inc. (Helsinki, Finland) and AMF Bruns GmbH (Apens, Germany).

Multi-Train Processes

In the processes of the invention, each process may be performed in one or more processing units. For example, one or more hydromethanation reactors may be supplied with the carbonaceous feedstock from one or more catalyst loading and/or feedstock preparation unit operations. Similarly, the methane-enriched raw product streams generated by one or more hydromethanation reactors may be processed or purified separately or via their combination at various downstream points depending on the particular system configuration, as discussed, for example, in previously incorporated US2009/0324458A1, US2009/0324459A1, US2009/0324460A1, US2009/0324461A1 and US2009/0324462A1.

In certain embodiments, the processes utilize two or more hydromethanation reactors (e.g., 2-4 hydromethanation reactors). In such embodiments, the processes may contain divergent processing units (i.e., less than the total number of hydromethanation reactors) prior to the hydromethanation reactors for ultimately providing the catalyzed carbonaceous feedstock to the plurality of hydromethanation reactors, and/or convergent processing units (i.e., less than the total number of hydromethanation reactors) following the hydromethanation reactors for processing the plurality of methane-enriched raw product streams generated by the plurality of hydromethanation reactors.

When the systems contain convergent processing units, each of the convergent processing units can be selected to have a capacity to accept greater than a 1/n portion of the total feed stream to the convergent processing units, where n is the number of convergent processing units. Similarly, when the systems contain divergent processing units, each of the divergent processing units can be selected to have a capacity to accept greater than a 1/m portion of the total feed stream supplying the convergent processing units, where m is the number of divergent processing units.

Examples of Specific Embodiments

In one embodiment, the screw discharge unit is a cooling screw discharge unit, the gas-stripped char stream is cooled in the cooling screw discharge unit to generate a cooled char stream, and the cooled char stream is discharged from the cooled screw discharge unit at a temperature of about 700° F. (about 371° C.) or less.

In another embodiment, the cooling screw discharge unit cools the gas-stripped char stream using water or steam as a heat exchange medium. In another embodiment, the cooling screw unit comprises a hollow screw member and a housing surrounding the hollow screw member, wherein the heat exchange medium is circulated through the hollow screw member, around the housing or both.

In another embodiment, the stripping gas comprises steam, carbon dioxide or both. In yet another embodiment, the stripping gas additionally comprises oxygen.

In still another embodiment, the gas-stripped char stream (or the cooled char stream if present) is discharged from the screw discharge unit into a quench tank. In yet another embodiment, the gas-stripped char is contacted with a quench medium in the quench tank.

In another embodiment, the gas-stripped char stream (or cooled char stream if present) is discharged from the screw discharge unit at a superatmospheric pressure of at least of at least about 75%, or at least about 90%, of the operating pressure of the hydromethanation reactor.

In another embodiment, the carbonaceous feedstock is reacted in the hydromethanation reactor in the presence of carbon monoxide, hydrogen, steam, oxygen and hydromethanation catalyst.

We claim:

1. A process for generating a methane-enriched raw product gas stream and a gas-stripped char stream from a non-gaseous carbonaceous material, the process comprising the steps of:
   (a) preparing a carbonaceous feedstock from the non-gaseous carbonaceous material;
   (b) introducing the carbonaceous feedstock and a hydromethanation catalyst into a hydromethanation reactor, wherein the hydromethanation reactor comprises a char-withdrawal standpipe having a withdrawal end extending into the hydromethanation reactor and a discharge end extending out of the hydromethanation reactor;
   (c) reacting the carbonaceous feedstock in the hydromethanation reactor in the presence of carbon monoxide, hydrogen, steam and hydromethanation catalyst, and at an operating temperature of at least about 1000° F. (at least about 538° C.) and an operating pressure of at least about 250 psig (about 1825 kPa) to produce a methane-enriched raw product gas and a solid by-product char;
   (d) withdrawing a stream of the methane-enriched raw product gas from the hydromethanation reactor as the methane-enriched raw product gas stream, wherein the methane-enriched raw product gas stream comprises methane, carbon monoxide, hydrogen, carbon dioxide, hydrogen sulfide, steam and heat energy;
   (e) withdrawing a stream of the solid by-product char from the hydromethanation reactor via the withdrawal end of the char-withdrawal standpipe, wherein the stream of solid by-product char flows from the withdrawal end to the discharge end of the char-withdrawal standpipe, and wherein the withdrawn solid by-product char comprises an entrained gas;
   (f) feeding a stripping gas into the char-withdrawal standpipe such that the stripping gas flows in a countercurrent direction to the flow of the stream of by-product char within the char-withdrawal standpipe to generate (1) a stripped gas stream enriched in the entrained gas and (2) a gas-stripped char stream depleted in the entrained gas;
   (g) feeding the stripped gas stream into the hydromethanation reactor via the char-withdrawal standpipe;
   (h) feeding the gas-stripped char stream to a screw discharge unit in communication with the discharge end of the char-withdrawal standpipe;
   (i) discharging the gas-stripped char stream from the screw discharge unit at a superatmospheric pressure.

2. The process of claim 1, wherein the screw discharge unit is a cooling screw discharge unit, and the gas-stripped char stream is cooled in the cooling screw discharge unit to generate a cooled char stream.

3. The process of claim 2, wherein the cooling char stream is discharged from the cooled screw discharge unit at a temperature of about 700° F. (about 371° C.) or less.

4. The process of claim 2, wherein the cooling screw discharge unit cools the gas-stripped char stream using water or steam as a heat exchange medium.

5. The process of claim 4, wherein the cooling screw discharge unit comprises a hollow screw member and a housing surrounding the hollow screw member, wherein the heat exchange medium is circulated through the hollow screw member.

6. The process of claim 1, wherein the stripping gas comprises steam, carbon dioxide or both.

7. The process of claim 6, wherein the stripping gas additionally comprises oxygen.

8. The process of claim 1, wherein the gas-stripped char stream is discharged from the screw discharge unit into a quench tank and contacted with a quench medium in the quench tank.

9. The process of claim 1, wherein the gas-stripped char stream is discharged from the screw discharge unit at a superatmospheric pressure of at least of at least about 75% of the operating pressure of the hydromethanation reactor.

10. The process of claim 8, wherein the gas-stripped char stream is discharged from the screw discharge unit at a superatmospheric pressure of at least about 75% of the operating pressure of the hydromethanation reactor.

11. The process of claim 2, wherein the cooled char stream is discharged from the screw discharge unit into a quench tank and contacted with a quench medium in the quench tank.

12. The process of claim 2, wherein the cooled char stream is discharged from the screw discharge unit at a superatmospheric pressure of at least about 75% of the operating pressure of the hydromethanation reactor.

13. The process of claim 11, wherein the cooled char stream is discharged from the screw discharge unit at a superatmospheric pressure of at least about 75% of the operating pressure of the hydromethanation reactor.

14. The process of claim 1, wherein in step (c) the carbonaceous feedstock is reacted in the hydromethanation reactor in the presence of carbon monoxide, hydrogen, steam, oxygen and hydromethanation catalyst.

15. The process of claim 1, wherein in step (c) the operating temperature is to about 1500° F. (about 816° C.).

16. The process of claim 1, wherein the operating pressure is to about 1000 psig (about 6996 kPa).

* * * * *